US010808022B2

(12) United States Patent
Bechard et al.

(10) Patent No.: US 10,808,022 B2
(45) Date of Patent: Oct. 20, 2020

(54) IL-15/IL-15RALPHA BASED CONJUGATES PURIFICATION METHOD

(71) Applicant: Cytune Pharma, Nantes (FR)

(72) Inventors: David Bechard, Saint-Etienne de Montluc (FR); Guy de Martynoff, Mont-Saint-Guibert (BE)

(73) Assignee: Cytune Pharma, Nantes (FR)

( * ) Notice: Subject to any disclaimer, the term of this patent is extended or adjusted under 35 U.S.C. 154(b) by 124 days.

(21) Appl. No.: 15/123,153

(22) PCT Filed: Mar. 3, 2015

(86) PCT No.: PCT/EP2015/000473
§ 371 (c)(1),
(2) Date: Sep. 1, 2016

(87) PCT Pub. No.: WO2015/131994
PCT Pub. Date: Sep. 11, 2015

(65) Prior Publication Data
US 2017/0056874 A1    Mar. 2, 2017

(30) Foreign Application Priority Data

Mar. 3, 2014 (EP) .................................... 14000742

(51) Int. Cl.
| | |
|---|---|
| C07K 14/705 | (2006.01) |
| C07K 14/715 | (2006.01) |
| B01D 15/32 | (2006.01) |
| B01D 15/36 | (2006.01) |
| C07K 14/54 | (2006.01) |
| B01D 15/14 | (2006.01) |
| B01J 41/20 | (2006.01) |
| C07K 1/18 | (2006.01) |
| C07K 1/20 | (2006.01) |
| A61K 38/00 | (2006.01) |

(52) U.S. Cl.
CPC .......... C07K 14/7155 (2013.01); B01D 15/14 (2013.01); B01D 15/327 (2013.01); B01D 15/363 (2013.01); B01J 41/20 (2013.01); C07K 1/18 (2013.01); C07K 1/20 (2013.01); C07K 14/5443 (2013.01); A61K 38/00 (2013.01); C07K 2319/00 (2013.01)

(58) Field of Classification Search
None
See application file for complete search history.

(56) References Cited

U.S. PATENT DOCUMENTS

| | | | |
|---|---|---|---|
| 4,671,958 A | 6/1987 | Rodwell et al. | |
| 5,011,912 A | 4/1991 | Hopp et al. | |
| 5,073,627 A | 12/1991 | Curtis et al. | |
| 5,108,910 A | 4/1992 | Curtis et al. | |
| 5,225,539 A | 7/1993 | Winter | |
| 5,558,864 A | 9/1996 | Bendig et al. | |
| 5,585,089 A | 12/1996 | Queen et al. | |
| 5,595,721 A | 1/1997 | Kaminski et al. | |
| 5,645,835 A | 7/1997 | Fell, Jr. et al. | |
| 5,677,171 A | 10/1997 | Hudziak et al. | |
| 5,730,969 A | 3/1998 | Hora et al. | |
| 5,736,137 A | 4/1998 | Anderson et al. | |
| 5,821,337 A | 10/1998 | Carter et al. | |
| 6,235,883 B1 | 5/2001 | Jakobovits et al. | |
| 6,787,132 B1 | 9/2004 | Gabizon et al. | |
| 7,060,808 B1 | 6/2006 | Goldstein et al. | |
| 7,112,436 B1 | 9/2006 | Rose-John | |
| 7,186,804 B2 | 3/2007 | Gillies et al. | |
| 7,198,781 B1 | 4/2007 | Revel et al. | |
| 7,906,118 B2 | 3/2011 | Chang et al. | |
| 8,124,084 B2 | 2/2012 | Lefrancois et al. | |
| 8,217,149 B2 | 7/2012 | Irving et al. | |
| 8,287,865 B2 | 10/2012 | Hansen et al. | |
| 8,945,897 B2 * | 2/2015 | Siekmann ........ | A61K 47/48038 435/188 |
| 9,714,296 B2 | 7/2017 | Johnson et al. | |
| 2005/0169932 A1 | 8/2005 | Cheung | |
| 2006/0025885 A1 | 2/2006 | Stefﬂ et al. | |
| 2006/0236411 A1 | 10/2006 | Dreher et al. | |
| 2009/0105455 A1 | 4/2009 | Herrmann | |

(Continued)

FOREIGN PATENT DOCUMENTS

| | | |
|---|---|---|
| EP | 0305967 A2 | 3/1989 |
| EP | 0439095 A2 | 7/1991 |

(Continued)

OTHER PUBLICATIONS

International Search Report and Written opinion for International Application No. PCT/EP2015/000473, dated May 26, 2015 (12 pages).

Han et al., "IL-15:IL-15 receptor alpha superagonsit complex: High-level co-expression in recombinant mammalian cells, purification and characterization", Cytokine, Academic Press Ltd, vol. 56, No. 3, Sep. 28, 2011, pp. 804-810.

Bessard et al., "High antitumor activity of RLI, and interleukin-15 (IL-15)-IL-15 receptor a fusion protein, in metastatic melanoma and colorectal cancer", Molecular Cancer Therapeutics, American Association of Cancer Research, vol. 8, No. 9, Sep. 1, 2009, pp. 2736-2745.

(Continued)

*Primary Examiner* — Michael D Pak
(74) *Attorney, Agent, or Firm* — Kagan Binder, PLLC

(57) ABSTRACT

The present invention relates to a method for preparing a composition comprising monomeric conjugates from a sample, said conjugate comprising (a) a polypeptide comprising the amino acid sequence of interleukin 15 or derivatives thereof, and (b) a polypeptide comprising the amino acid sequence of the sushi domain of IL-15Rα or derivatives thereof; wherein said method comprises the use of anion-exchange chromatography followed by a hydrophobic interaction chromatography; and to a pharmaceutical composition which can be obtained by such a method.

10 Claims, 7 Drawing Sheets

Specification includes a Sequence Listing.

(56) References Cited

U.S. PATENT DOCUMENTS

| | | |
|---|---|---|
| 2009/0238791 A1 | 9/2009 | Jacques et al. |
| 2010/0143245 A1 | 6/2010 | Cheung |
| 2010/0150910 A1 | 6/2010 | Birkle et al. |
| 2010/0310501 A1 | 12/2010 | Boyman et al. |
| 2012/0177595 A1* | 7/2012 | Wong ................ C07K 14/5443 424/85.2 |
| 2012/0190096 A1 | 7/2012 | Siekmann et al. |
| 2012/0244118 A1 | 9/2012 | Berraondo Lopez et al. |
| 2013/0164251 A1 | 6/2013 | Wen et al. |
| 2015/0359853 A1 | 12/2015 | Felber et al. |
| 2016/0318986 A1 | 11/2016 | Morisseau et al. |

FOREIGN PATENT DOCUMENTS

| | | |
|---|---|---|
| EP | 1777294 A1 | 4/2007 |
| GB | 2188638 A | 10/1987 |
| WO | 8500974 | 3/1985 |
| WO | 8601533 | 3/1986 |
| WO | 9215683 | 9/1992 |
| WO | 199527722 | 10/1995 |
| WO | 0047228 | 8/2000 |
| WO | 0158957 | 8/2001 |
| WO | 0187330 A2 | 11/2001 |
| WO | 0222805 A2 | 3/2002 |
| WO | 02072605 A2 | 9/2002 |
| WO | 2004035607 A2 | 4/2004 |
| WO | 2005085282 A1 | 9/2005 |
| WO | 2007001677 A2 | 1/2007 |
| WO | 2007046006 A2 | 4/2007 |
| WO | 2007084342 A2 | 7/2007 |
| WO | 2007128563 A1 | 11/2007 |
| WO | 2008143794 A1 | 11/2008 |
| WO | 2009002562 A2 | 12/2008 |
| WO | 2009012600 A1 | 1/2009 |
| WO | 2009135031 A1 | 11/2009 |
| WO | 2012175222 A1 | 12/2012 |
| WO | 2012178137 A1 | 12/2012 |
| WO | 2014170032 A1 | 10/2014 |
| WO | 2015018528 A1 | 2/2015 |
| WO | 2015018529 A1 | 2/2015 |

OTHER PUBLICATIONS

Bouchaud et al., "The Exon-3-Encoded Domain of IL-15Rα Contributes to IL-15 High-Affinity Binding and Is Crucial for the IL-15 Antagonistic Effect of Soluble IL-15Rα", Journal of Molecular Biology, vol. 382, No. 1, Sep. 26, 2008, pp. 1-12.

Mortier et al., "Soluble Interleukin-15 Receptor α (IL-15Rα)-sushi as a Selective and Potent Agonist of IL-15 Action through IL-15Rβ/γ", The Journal of Biological Chemistry, vol. 281, No. 3, Jan. 20, 2006, pp. 1612-1619.

Gluck, W. L., et al. (2004). "Phase I studies of interleukin (IL)-2 and rituximab in B-cell non-hodgkin's lymphoma: IL-2 mediated natural killer cell expansion correlations with clinical response." Clin Cancer Res 10(7): 2253-2264.

Halin, C., et al. (2002). "Enhancement of the antitumor activity of interleukin-12 by targeted delivery to neovasculature." Nat Biotechnol 20(3): 264-269.

Handgretinger, R., et al. (1995). "A phase I study of human/mouse chimeric antiganglioside GD2 antibody ch14.18 in patients with neuroblastoma." Eur J Cancer 31A(2): 261-267.

Imai, M., et al. (2005). "Complement-mediated mechanisms in anti-GD2 monoclonal antibody therapy of murine metastatic cancer." Cancer Res 65(22): 10562-10568.

Kaspar, M., et al. (2007). "The antibody-mediated targeted delivery of interleukin-15 and GM-CSF to the tumor neovasculature inhibits tumor growth and metastasis." Cancer Res 67(10): 4940-4948.

Kendra, K., et al. (1999). "Pharmacokinetics and stability of the ch14.18-interleukin-2 fusion protein in mice." Cancer Immunol Immunother 48(5): 219-229.

Kermer, V., et al. (2010). Antibody fusion proteins for cancer immunotherapy mimicking IL-15 trans presentation at the tumor site. CIMT Cancer Immunotherapy 8th annual meeting, CIMT abstract book 2010: abstract No. 113, 163.

Kermer, V., et al. (2012). "An antibody fusion protein for cancer immunotherapy mimicking IL-15 trans-presentation at the tumor site." Mol Cancer Ther 11(6): 1279-1288.

Kontermann, R. E. (2012). "Antibody-cytokine fusion proteins." Arch Biochem Biophys 526(2): 194-205.

Laprevotte, E., et al. (2013). "Recombinant human IL-15 transpresentation by B leukemic cells from chronic lymphocytic leukemia induces autologous NK cell proliferation leading to improved anti-CD20 immunotherapy." J Immunol 191(7): 3634-3640.

Lazar, E., et al. (1988). "Transforming growth factor alpha: mutation of aspartic acid 47 and leucine 48 results in different biological activities." Mol Cell Biol 8(3): 1247-1252.

Lode, H. N. and R. A. Reisfeld (2000). "Targeted cytokines for cancer immunotherapy." Immunol Res 21(2-3): 279-288.

Lode, H. N., et al. (1997). "Targeted interleukin-2 therapy for spontaneous neuroblastoma metastases to bone marrow." J Natl Cancer Inst 89(21): 1586-1594.

Mueller, B. M., et al. (1990). "Enhancement of antibody-dependent cytotoxicity with a chimeric anti-GD2 antibody." J Immunol 144(4): 1382-1386.

Munger, W., et al. (1995). "Studies evaluating the antitumor activity and toxicity of interleukin-15, a new T cell growth factor: comparison with interleukin-2." Cell Immunol 165(2): 289-293.

NCBI database entry for IL-15 accession No. NP_000576.1, downloaded Mar. 28, 2017 from http://www.ncbi.nlm.nih.gov/protein/NP_000576.1 ).

Ortiz-Sanchez, E., et al. (2008). "Antibody-cytokine fusion proteins: applications in cancer therapy." Expert Opin Biol Ther 8(5): 609-632.

Pasche, N. and D. Neri (2012). "Immunocytokines: a novel class of potent armed antibodies." Drug Discov Today 17(11-12): 583-590.

Penichet, M. L and S. L. Morrison (2001). "Antibody-cytokine fusion proteins for the therapy of cancer." J Immunol Methods 248(1-2): 91-101.

Reif, M. E., et al. (1994). "Depletion of B cells in vivo by a chimeric mouse human monoclonal antibody to CD20." Blood 83(2): 435-445.

Riechmann, L., et al. (1988). "Reshaping human antibodies for therapy." Nature 332(6162): 323-327.

Ronca, R., et al. (2009). "Delivering cytokines at tumor site: The immunocytokine-conjugated anti-EDB-fibronectin antibody case." Immunobiology 214(9-10): 800-810.

Singh, H., et al. (2007). "Combining adoptive cellular and immunocytokine therapies to improve treatment of B-lineage malignancy." Cancer Res 67(6): 2872-2880.

Svennerholm, L., et al. (1994). "Membrane lipids of adult human brain: lipid composition of frontal and temporal lobe in subjects of age 20 to 100 years." J Neurochem 63(5): 1802-1811.

Till, M. A., et al. (1989). "Human immunodeficiency virus-infected T cells and monocytes are killed by monoclonal human anti-gp41 antibodies coupled to ricin A chain." Proc Natl Acad Sci U S A 86(6): 1987-1991.

Tran, M., et al. (2008). "Targeting a tumor-specific laminin domain critical for human carcinogenesis." Cancer Res 68(8): 2885-2894.

Vajdos, F. F., et al. (2002). "Comprehensive functional maps of the antigen-binding site of an anti-ErbB2 antibody obtained with shotgun scanning mutagenesis." J Mol Biol 320(2): 415-428.

Xuan, C., et al. (2010). "Targeted delivery of interferon-alpha via fusion to anti-CD20 results in potent antitumor activity against B-cell lymphoma." Blood 115(14): 2864-2871.

Yuki, N., et al. (1997). "Pathogenesis of the neurotoxicity caused by anti-GD2 antibody therapy." J Neurol Sci 149(2): 127-130.

Zago, P., et al. (2009). "Improving human interferon-beta production in mammalian cell lines by insertion of an intronic sequence within its naturally uninterrupted gene." Biotechnol Appl Biochem 52(Pt 3): 191-198.

Johannsen, M., et al. (2010). "The tumour-targeting human L19-IL2 immunocytokine: preclinical safety studies, phase I clinical trial in

(56) References Cited

OTHER PUBLICATIONS patients with solid tumours and expansion into patients with advanced renal cell carcinoma." Eur J Cancer 46(16): 2926-2935.
Giron-Michel, J., et al. (2005). "Membrane-bound and soluble IL-15/IL-15Ralpha complexes display differential signaling and functions on human hematopoietic progenitors." Blood 106(7): 2302-2310.
Matsumoto, M., et al. (2003). "On-column refolding and characterization of soluble human interleukin-15 receptor alpha-chain produced in *Escherichia coli*." Protein Expr Purif 31(1): 64-71.
Ruchatz, H., et al. (1998). "Soluble IL-15 receptor alpha-chain administration prevents murine collagen-induced arthritis: a role for IL-15 in development of antigen-induced immunopathology." J Immunol 160(11): 5654-5660.
Giri, J. G., et al. (1994). "Utilization of the beta and gamma chains of the IL-2 receptor by the novel cytokine IL-15." EMBO J 13(12): 2822-2830.
Anderson, D. M., et al. (1995). "Functional characterization of the human interleukin-15 receptor alpha chain and close linkage of IL15RA and IL2RA genes." J Biol Chem 270(50): 29862-29869.
Burton, J. D., et al. (1994). "A lymphokine, provisionally designated interleukin T and produced by a human adult T-cell leukemia line, stimulates T-cell proliferation and the induction of lymphokine-activated killer cells." Proc Natl Acad Sci U S A 91(11): 4935-4939.
Carson, W. E., et al. (1994). "Interleukin (IL) 15 is a novel cytokine that activates human natural killer cells via components of the IL-2 receptor." J Exp Med 180(4): 1395-1403.
Wilkinson, P. C. and F. Y. Liew (1995). "Chemoattraction of human blood T lymphocytes by interleukin-15." J Exp Med 181(3): 1255-1259.
Kennedy, M. K., et al. (2000). "Reversible defects in natural killer and memory CD8 T cell lineages in interleukin 15-deficient mice." J Exp Med 191(5): 771-780.
Lodolce, J. P., et al. (2001). "T cell-independent interleukin 15Ralpha signals are required for bystander proliferation." J Exp Med 194(8): 1187-1194.
Marks-Konczalik, J., et al. (2000). "IL-2-induced activation-induced cell death is inhibited in IL-15 transgenic mice." Proc Natl Acad Sci U S A 97(21): 11445-11450.
Ku, C. C., et al. (2000). "Control of homeostasis of CD8+ memory T cells by opposing cytokines." Science 288(5466): 675-678.
Li, X. C., et al. (2001). "IL-15 and IL-2: a matter of life and death for T cells in vivo." Nat Med 7(1): 114-118.
Dubois, S., et al. (2002). "IL-15Ralpha recycles and presents IL-15 in trans to neighboring cells." Immunity 17(5): 537-547.
Burkett, P. R., et al. (2003). "IL-15Rα expression on CD8+ T cells is dispensable for T cell memory." Proc Natl Acad Sci U S A 100(8): 4724-4729.
Schluns, K. S., et al. (2004). "Distinct cell types control lymphoid subset development by means of IL-15 and IL-15 receptor alpha expression." Proc Natl Acad Sci U S A 101(15): 5616-5621.
Kobayashi, H., et al. (2005). "Role of trans-cellular IL-15 presentation in the activation of NK cell-mediated killing, which leads to enhanced tumor immunosurveillance." Blood 105(2): 721-727.
Norman, D. G., et al. (1991). "Three-dimensional structure of a complement control protein module in solution." J Mol Biol 219(4): 717-725.
Schulz, O., et al. (1998). "Proteolytic cleavage of CD25, the alpha subunit of the human T cell interleukin 2 receptor, by Der p 1, a major mite allergen with cysteine protease activity." J Exp Med 187(2): 271-275.
Sheu, B. C., et al. (2001). "A novel role of metalloproteinase in cancer-mediated immunosuppression." Cancer Res 61(1): 237-242.
Smith, X. G., et al. (2000). "Selective blockade of IL-15 by soluble IL-15 receptor alpha-chain enhances cardiac allograft survival." J Immunol 165(6): 3444-3450.
Farner, N. L., et al. (1997). "Alteration of the CD34+ Tf-1 beta cell line profile in response to long-term exposure to IL-15." Cytokine 9(5): 316-327.

Meissner, U., et al. (2001). "A soluble form of the murine common gamma chain is present at high concentrations in vivo and suppresses cytokine signaling." Blood 97(1): 183-191.
Jones, S. A. and S. Rose-John (2002). "The role of soluble receptors in cytokine biology: the agonistic properties of the sIL-6R/IL-6 complex." Biochim Biophys Acta 1592(3): 251-263.
Heaney, M. L. and D. W. Golde (1998). "Soluble receptors in human disease." J Leukoc Biol 64(2): 135-146.
Rose-John, S. and P. C. Heinrich (1994). "Soluble receptors for cytokines and growth factors: generation and biological function." Biochem J 300 ( Pt 2): 281-290.
Davis, S., et al. (1993). "Released form of CNTF receptor alpha component as a soluble mediator of CNTF responses." Science 259(5102): 1736-1739.
Karow, J., et al. (1996). "Mediation of interleukin-11-dependent biological responses by a soluble form of the interleukin-11 receptor." Biochem J 318 ( Pt 2): 489-495.
Elson, G. C., et al. (2000). "CLF associates with CLC to form a functional heteromeric ligand for the CNTF receptor complex." Nat Neurosci 3(9): 867-872.
Sandau, M. M., et al. (2004). "Cutting edge: transpresentation of IL-15 by bone marrow-derived cells necessitates expression of IL-15 and IL-15R alpha by the same cells." J Immunol 173(11): 6537-6541.
Koka, R., et al. (2003). "Interleukin (IL)-15R□-deficient natural killer cells survive in normal but not IL-15R□-deficient mice." J Exp Med 197(8): 977-984.
Bulanova, E., et al. (2003). "Mast cells express novel functional IL-15 receptor alpha isoforms." J Immunol 170(10): 5045-5055.
Fischer, M., et al. (1997). "I. A bioactive designer cytokine for human hematopoietic progenitor cell expansion." Nat Biotechnol 15(2): 142-145.
Hopp, T. P., et al. (1988). "A short polypeptide marker sequence useful for recombinant protein identification and purification." Biotechnology 6(10): 1204-1210.
Andersson, L., et al. (2000). "Large-scale synthesis of peptides." Biopolymers 55(3): 227-250.
Fernandez-Botran, R. (1991). "Soluble cytokine receptors: their role in immunoregulation." FASEB J 5(11): 2567-2574.
Pettitt, D. K., et al. (1997). "Structure-function studies of interleukin 15 using site-specific mutagenesis, polyethylene glycol conjugation, and homology modeling." J Biol Chem 272(4): 2312-2318.
Forcina, G., et al. (2004). "Interleukin-15 modulates interferon-gamma and beta-chemokine production in patients with HIV infection: implications for immune-based therapy." Cytokine 25(6): 283-290.
Budagian, V., et al. (2004). "Natural soluble interleukin-15R□ is generated by cleavage that involves the tumor necrosis factor-□-converting enzyme (TACE/ADAM17)." J Biol Chem 279(39): 40368-40375.
Rubinstein, M. P., et al. (2006). "Converting IL-15 to a superagonist by binding to soluble IL-15R□." Proc Natl Acad Sci U S A 103(24): 9166-9171.
Kanakura, Y., et al. (1993). "Functional expression of interleukin 2 receptor in a human factor-dependent megakaryoblastic leukemia cell line: evidence that granulocyte-macrophage colony-stimulating factor inhibits interleukin 2 binding to its receptor." Cancer Res 53(3): 675-680.
Carson, W. and M. A. Caligiuri (1998). "Interleukin-15 as a potential regulator of the innate immune response." Braz J Med Biol Res 31(1): 1-9.
Bamford, R. N., et al. (1994). "The interleukin (IL) 2 receptor beta chain is shared by IL-2 and a cytokine, provisionally designated IL-T, that stimulates T-cell proliferation and the induction of lymphokine-activated killer cells." Proc Natl Acad Sci U S A 91(11): 4940-4944.
Avanzi, G. C., et al. (1988). "Selective growth response to IL-3 of a human leukaemic cell line with megakaryoblastic features." Br J Haematol 69(3): 359-366.
Margolin, K. A. (2000). "Interleukin-2 in the treatment of renal cancer." Semin Oncol 27(2): 194-203.
Meazza R. et al.(2011). "Role of common-gamma chain cytokines in NK cell development and function: perspectives for immunotherapy." J Biomed Biotechnol 2011: 861920.

(56) References Cited

OTHER PUBLICATIONS

Rosenberg, S. A., et al. (1994). "Treatment of patients with metastatic melanoma with autologous tumor-infiltrating lymphocytes and interleukin 2." J Natl Cancer Inst 86(15): 1159-1166.
Eklund, J. W. and T. M. Kuzel (2004). "A review of recent findings involving interleukin-2-based cancer therapy." Curr Opin Oncol 16(6): 542-546.
Guo, H. and X. Qian (2010). "Clinical applications of adoptive natural killer cell immunotherapy for cancer: current status and future prospects." Onkologie 33(7): 389-395.
Hallett, W. H. and W. J. Murphy (2004). "Natural killer cells: biology and clinical use in cancer therapy." Cell Mol Immunol 1(1): 12-21.
Plautz, G. E., et al. (2003). "Considerations on clinical use of T cell immunotherapy for cancer." Arch Immunol Ther Exp (Warsz) 51(4): 245-257.
Schluns, K. S., et al. (2005). "The roles of interleukin-15 receptor alpha: trans-presentation, receptor component, or both?" Int J Biochem Cell Biol 37(8): 1567-1571.
Van Belle, T. and J. Grooten (2005). "IL-15 and IL-15Ralpha in CD4+T cell immunity." Arch Immunol Ther Exp (Warsz) 53(2): 115-126.
Ferrari-Lacraz, S., et al. (2004). "Targeting IL-15 receptor-bearing cells with an antagonist mutant IL-15/Fc protein prevents disease development and progression in murine collagen-induced arthritis." J Immunol 173(9): 5818-5826.
Oh, S., et al. (2004). "IL-15/IL-15Ralpha-mediated avidity maturation of memory CD8+ T cells." Proc Natl Acad Sci U S A 101(42): 15154-15159.
Schluns, K. S., et al. (2002). "Cutting edge: requirement for IL-15 in the generation of primary and memory antigen-specific CD8 T cells." J Immunol 168(10): 4827-4831.
Liu, K., et al. (2002). "IL-15 mimics T cell receptor crosslinking in the induction of cellular proliferation, gene expression, and cytotoxicity in CD8+ memory T cells." Proc Natl Acad Sci U S A 99(9): 6192-6197.
Olosz, F. and T. R. Malek (2002). "Structural basis for binding multiple ligands by the common cytokine receptor gamma-chain." J Biol Chem 277(14): 12047-12052.
Waldmann, T. A. (2002). "The IL-2/IL-15 receptor systems: targets for immunotherapy." J Clin Immunol 22(2): 51-56.
Ferrari-Lacraz, S., et al. (2001). "An antagonist IL-15/Fc protein prevents costimulation blockade-resistant rejection." J Immunol 167(6): 3478-3485.
Pereno, R., et al. (1999). "IL-15/IL-15R alpha intracellular trafficking in human cells and protection from apoptosis." Ann N Y Acad Sci 876: 236-245.
Prinz, M., et al. (1998). "Alternative splicing of mouse IL-15 is due to the use of an internal splice site in exon 5." Brain Res Mol Brain Res 63(1): 155-162.
Lodolce, J. P., et al. (1998). "IL-15 receptor maintains lymphoid homeostasis by supporting lymphocyte homing and proliferation." Immunity 9(5): 669-676.
Waldmann, T., et al. (1998). "Interleukin-2, interleukin-15, and their receptors." Int Rev Immunol 16(3-4): 205-226.
Ohteki, T., et al. (1997). "Role for IL-15/IL-15 receptor beta-chain in natural killer 1.1+ T cell receptor-alpha beta+ cell development." J Immunol 159(12): 5931-5935.
DiSanto, J. P. (1997). "Cytokines: shared receptors, distinct functions." Curr Biol 7(7): R424-426.
Kennedy, M. K. and L. S. Park (1996). "Characterization of interleukin-15 (IL-15) and the IL-15 receptor complex." J Clin Immunol 16(3): 134-143.
Cosman, D., et al. (1995). "Interleukin 15 and its receptor." Ciba Found Symp 195: 221-229; discussion 229-233.
Assier, E., et al. (2005). "Constitutive expression of IL-2Rbeta chain and its effects on IL-2-induced vascular leak syndrome." Cytokine 32(6): 280-286.

Grabstein, K. H., et al. "Cloning of a T Cell Growth Factor That Interacts with the β Chain of the Interleukin-2 Receptor." Science 264, No. 5161 (May 13, 1994): 965-8.
Hori, T., et al. "Establishment of an Interleukin 2-Dependent Human T Cell Line from a Patient with T Cell Chronic Lymphocytic Leukemia Who Is Not Infected with Human T Cell Leukemia/Lymphoma Virus." Blood 70, No. 4 (Oct. 1987): 1069-72.
Smith, Temple F., and Michael S. Waterman. "Comparison of Biosequences." Advances in Applied Mathematics 2, No. 4 (Dec. 1, 1981 1981): 482-89.
Needleman, S. B., and C. D. Wunsch. "A General Method Applicable to the Search for Similarities in the Amino Acid Sequence of Two Proteins." J Mol Biol 48, No. 3 (Mar. 1970): 443-53.
Pearson, W. R., and D. J. Lipman. "Improved Tools for Biological Sequence Comparison." Proc Natl Acad Sci U S A 85, No. 8 (Apr. 1988): 2444-8.
Edgar, R. C. "Muscle: Multiple Sequence Alignment with High Accuracy and High Throughput." Nucleic Acids Res 32, No. 5 (2004): 1792-7.
Zhu, X., et al. "Novel Human Interleukin-15 Agonists." Journal of Immunology, 183, No. 6 (Sep. 15, 2009): 3598-607.
Wei, Xq, et al. "The Sushi Domain of Soluble Il-15 Receptor Alpha Is Essential for Binding Il-15 and Inhibiting Inflammatory and Allogenic Responses in Vitro and in Vivo." Journal of Immunology, 167, No. 1 (Jul. 1, 2001): 277-82.
Gilman, A. L., et al. (2009). "Phase I study of ch14.18 with granulocyte-macrophage colony-stimulating factor and interleukin-2 in children with neuroblastoma after autologous bone marrow transplantation or stem-cell rescue: a report from the Children's Oncology Group." J Clin Oncol 27(1): 85-91.
Gillies, S. D., et al. (2005). "An anti-CD20-IL-2 immunocytokine is highly efficacious in a SCID mouse model of established human B lymphoma." Blood 105(10): 3972-3978.
Gillies, S. D., et al. (2002). "Improved circulating half-life and efficacy of an antibody-interleukin 2 immunocytokine based on reduced intracellular proteolysis." Clin Cancer Res 8(1): 210-216.
Gillies, S. D., et al. (1999). "Improving the efficacy of antibody-interleukin 2 fusion proteins by reducing their interaction with Fc receptors." Cancer Res 59(9): 2159-2166.
Nakamura, Y., et al. "Heterodimerization of the IL-2 Receptor Beta- and Gamma-Chain Cytoplasmic Domains Is Required for Signalling." Nature 369, No. 6478 (May 26, 1994): 330-3.
Cerato, Evelyne, et al. "Variable Region Gene Segments of Nine Monoclonal Antibodies Specific to Disialogangliosides (Gd2, Gd3) and Their O-Acetylated Derivatives." Hybridoma 16, No. 4 (Aug. 1, 1997 1997): 307-16.
Dubois, S., et al. "Natural Splicing of Exon 2 of Human Interleukin-15 Receptor Alpha-Chain Mrna Results in a Shortened Form with a Distinct Pattern of Expression." J Biol Chem 274, No. 38 (Sep. 17, 1999): 26978-84.
Pflanz, S., et al. "A Fusion Protein of Interleukin-11 and Soluble Interleukin-11 Receptor Acts as a Superagonist on Cells Expressing Gp130." FEBS Lett 450, No. 1-2 (Apr. 30, 1999): 117-22.
Lehours, P., et al. "Subunit Structure of the High and Low Affinity Human Interleukin-15 Receptors." Eur Cytokine Netw 11, No. 2 (Jun. 2000): 207-15.
Bernard, J., et al. "Identification of an Interleukin-15alpha Receptor-Binding Site on Human Interleukin-15." J Biol Chem 279, No. 23 (Jun. 4, 2004): 24313-22.
Mortier, E., et al. "Natural, Proteolytic Release of a Soluble Form of Human Il-15 Receptor Alpha-Chain That Behaves as a Specific, High Affinity Il-15 Antagonist." J Immunol 173, No. 3 (Aug. 1, 2004): 1681-8.
Lorenzen, I., et al. "The Structure of the Interleukin-15 Alpha Receptor and Its Implications for Ligand Binding." J Biol Chem 281, No. 10 (Mar. 10, 2006): 6642-7.
Quemener, A., et al. "Docking of Human Interleukin-15 to Its Specific Receptor Alpha Chain: Correlation between Molecular Modeling and Mutagenesis Experimental Data." Proteins 65, No. 3 (Nov. 15, 2006): 623-36.
Walzer, T., et al. "Natural Killer Cell Trafficking in Vivo Requires a Dedicated Sphingosine 1-Phosphate Receptor." Nat Immunol 8, No. 12 (Dec. 2007): 1337-44.

(56) References Cited

OTHER PUBLICATIONS

Badoual, C., et al. "The Soluble Alpha Chain of Interleukin-15 Receptor: A Proinflammatory Molecule Associated with Tumor Progression in Head and Neck Cancer." Cancer Res 68, No. 10 (May 15, 2008): 3907-14.
Bessard, A., et al. "High Antitumor Activity of Rli, an Il15-Il15ralpha Fusion Protein, in Metastatic Melanoma and Colorectal Cancer." In Tri-Society Annual Conference of the International-Cytokine-Society, Abstract: PP2-064. Lisbon: Abstract book, 2009.
Huntington, N. D., et al. "IL-15 Trans-Presentation Promotes Human Nk Cell Development and Differentiation in Vivo." J Exp Med 206, No. 1 (Jan. 16, 2009): 25-34.
Perdreau, H., et al. "Different Dynamics of Il-15r Activation Following Il-15 Cis- or Trans-Presentation." Eur Cytokine Netw 21, No. 4 (Dec. 2010): 297-307.
Huntington, N. D., et al. "Il-15 Transpresentation Promotes Both Human T-Cell Reconstitution and T-Cell-Dependent Antibody Responses in Vivo." Proc Natl Acad Sci U S A 108, No. 15 (Apr. 12, 2011): 6217-22 and Supporting Information, pp. 1-3.
Huntington, N. D., et al. "Autonomous and Extrinsic Regulation of Thymopoiesis in Human Immune System (His) Mice." Eur J Immunol 41, No. 10 (Oct. 2011): 2883-93.
Vincent, Marie, et al. "Cs14-6. Development of Two Il15 Immunocytokines Targeting Either Gd2- or Cd20-Tumoral Bearing Cells." Cytokine 56, No. 1 (Oct. 2011): 102.
Vincent, M., et al. "Tumor Targeting of the Il-15 Superagonist Rli by an Anti-Gd2 Antibody Strongly Enhances Its Antitumor Potency." Int J Cancer 133, No. 3 (Aug. 1, 2013): 757-65.
Vincent, M., et al. "Highly Potent Anti-Cd20-Rli Immunocytokine Targeting Established Human B Lymphoma in Scid Mouse." MAbs 6, No. 4 (Jul.-Aug. 2014): 1026-37.
Zhu, Baoquan, (2005) A book of New drug synthesis scheme design and preparation process new technology practice, 2168-2169.
Alvarez-Rueda, N., et al. (2007). "Binding activities and antitumor properties of a new mouse/human chimeric antibody specific for GD2 ganglioside antigen." Clin Cancer Res 13(18 Pt 2): 5613s-5620s.
Aubry, J. (1997). "8B6 Anti-O-Acetyl GD2 Ganglioside." Hybridoma 16(6): 568-568.
Baker, M. & Carr, F. 2010. Pre-clinical considerations in the assessment of immunogenicity for protein therapeutics. Curr Drug Saf, 5, 308-13.
Birkle, S., et al. (2003). "Role of tumor-associated gangliosides in cancer progression." Biochimie 85(3-4): 455-463.
Bowie, J. U., et al. (1990). "Deciphering the message in protein sequences: tolerance to amino acid substitutions." Science 247(4948): 1306-1310.
Brown, M., et al. (1996). "Tolerance of single, but not multiple, amino acid replacements in antibody VH CDR 2: a means of minimizing B cell wastage from somatic hypermutation?" J Immunol 156(9): 3285-3291.
Burgess, W. H., et al. (1990). "Possible dissociation of the heparin-binding and mitogenic activities of heparin-binding (acidic fibroblast) growth factor-1 from its receptor-binding activities by site-directed mutagenesis of a single lysine residue." J Cell Biol 111(5 Pt 1): 2129-2138.
Cahan, L. D., et al. (1982). "Identification of a human neuroectodermal tumor antigen (OFA-I-2) as ganglioside GD2." Proc Natl Acad Sci U S A 79(24): 7629-7633.
Campos-da-Paz, M., et al. (2008). "Production of recombinant human factor VIII in different cell lines and the effect of human XBP1 co-expression." Mol Biotechnol 39(2): 155-158.
Cheever, M. A., et al. (2009). "The prioritization of cancer antigens: a national cancer institute pilot project for the acceleration of translational research." Clin Cancer Res 15(17): 5323-5337.
Co, M. S., et al. (1991). "Humanized antibodies for antiviral therapy." Proc Natl Acad Sci U S A 88(7): 2869-2873.

Dubois, S., et al. (2008). "Preassociation of IL-15 with IL-15R alpha-IgG1-Fc enhances its activity on proliferation of NK and CD8+/CD44high T cells and its antitumor action." J Immunol 180(4): 2099-2106.
Eisenbeis, C. F., et al. (2004). "Combination immunotherapy of B-cell non-Hodgkin's lymphoma with rituximab and interleukin-2: a preclinical and phase I study." Clin Cancer Res 10(18 Pt 1): 6101-6110.
Epardaud, M., et al. (2008)."Interleukin-15/interleukin-15R alpha complexes promote destruction of established tumors by reviving tumor-resident CD8+ T cells." Cancer Res 68(8): 2972-2983.
Baoquan, Z., (2005) A Book of New Drug Synthesis Scheme Design and Preparation Process New Technology Practice, pp. 2166-2169 (English translation attached, 4 pages).
Kottke, T., et al. (2008). "Treg Depletion-enhanced IL-2 Treatment Facilitates Therapy of Established Tumors Using Systemically Delivered Oncolytic Virus." Mol Ther 16(7): 1217-1226.
Fyfe, G., et al. (1995). "Results of treatment of 255 patients with metastatic renal cell carcinoma who received high-dose recombinant interleukin-2 therapy." J Clin Oncol 13(3): 688-696.
Stone, J. D., A. S. Chervin, H. Schreiber and D. M. Kranz (2012). "Design and characterization of a protein superagonist of IL-15 fused with IL-15Ralpha and a high-affinity T cell receptor." Biotechnol Prog 28(6): 1588-1597.
Yu, P., et al. (2010). "Simultaneous blockade of multiple immune system inhibitory checkpoints enhances antitumor activity mediated by interleukin-15 in a murine metastatic colon carcinoma model." Clin Cancer Res 16(24): 6019-6028.
Steel, J. C., et al. (2012). "Interleukin-15 biology and its therapeutic implications in cancer." Trends Pharmacol Sci 33(1): 35-41.
Carson, W. E., 3rd (2010). "Braking bad: blockade of inhibitory pathways improves interleukin-15 therapy." Clin Cancer Res 16(24): 5917-5919.
Xu, W., et al. (2013). "Efficacy and mechanism-of-action of a novel superagonist interleukin-15: interleukin-15 receptor alphaSu/Fc fusion complex in syngeneic murine models of multiple myeloma." Cancer Res 73(10): 3075-3086.
Suh, W. K., et al. (2003). "The B7 family member B7-H3 preferentially down-regulates T helper type 1-mediated immune responses." Nat Immunol 4(9): 899-906.
Duraiswamy, J., et al. (2013). "Dual blockade of PD-1 and CTLA-4 combined with tumor vaccine effectively restores T-cell rejection function in tumors." Cancer Res 73(12): 3591-3603.
Hamanishi, J., et al. (2016). "PD-1/PD-L1 blockade in cancer treatment: perspectives and issues." Int J Clin Oncol 21(3): 462-473.
Mittica, G., et al. (2016). "Immune Checkpoint Inhibitors: A New Opportunity in the Treatment of Ovarian Cancer?" Int J Mol Sci 17(7).
Stoklasek, T. A., et al. (2006). "Combined IL-15/IL-15Ralpha immunotherapy maximizes IL-15 activity in vivo." J Immunol 177(9): 6072-6080.
Giri, J. G., et al. (1995). "Identification and cloning of a novel IL-15 binding protein that is structurally related to the alpha chain of the IL-2 receptor." EMBO J 14(15): 3654-3663.
Kikkawa et al. (1998) "Extraction and Separation Purification", Protein Experiment Notebook, vol. 1, pp. 107-112. (English translation of relevant parts of Kikkawa et al., 8 pages).
Office Action for Japanese Application No. 2016-555459, dated Aug. 20, 2019, 10 pages.
Yu et al. (2010) "Simultaneous Blockade of Multiple Immune System Inhibitory Checkpoints Enhances Antitumor Activity Mediated by Interleukin-15 in a Murine Metastatic Colon Carcinoma Model", Clinical Cancer Research, 16 (24):6019-6028.
Vincent et al. (2013) "Tumor targeting of the IL-15 superagonist RLI by an anti-GD2 antibody strongly enhances its antitumor potency", International Journal of Cancer, 133:757-765.
Vincent et al. (2011) "Development of two IL15 immunocytokines targeting either GD2- or CD20- tumoral bearing cells", Cytokinem 56, p. 102 (Abstract).
Xu et al. (2013) "Efficacy and Mechanism-of-Action of a Novel Superagonist Interleukin-15: Interleukin-15 Receptor aSu/Fc Fusion

(56) References Cited

OTHER PUBLICATIONS

Complex in Syngeneic Murine Models of Multiple Myeloma", Cancer Research, 73(10):3075-3086 (Supplementary Material, pp. 1-4).

Xu et al. (2012) "The tumor immunosuppressive microenvironment impairs the therapy of anti-HER2/neu antibody", Protien Cells, 3(6):441-449.

Bessard et al. (2009) "High antitumor activity of RU, an interleukin-15 (II-15)-IL-15 receptor a fusion protein, in metastatic melanoma and colorectal cancer", Molecular Cancer Therapeutics, 8(9):2736-2745.

Kermer et al. (2012) "An Antibody Fusion Protein for Cancer Immunotherapy Mimicking IL-15 trans-Presentation at the Tumor Site" Molecular Cancer Therapeutics, 11(6):1279-1288.

Yu et al. (2012) "Simultaneous inhibition of two regulatory T-cell subsets enhanced Interleukin-15 efficacy in a prostate tumor model", PNAS, 109(16):6187-6192.

Monier et al (2006) "Soluble Interleukin-15 Receptor a (IL-1 SRa)-sushi as a Selective and Potent Agonist of IL-15 Action through IL-15R beta/gamma", The Journal of Biological Chemistry, 281(3):1612-1619.

"PubChem Record Pidilizumab", SID 223366026—PubChem, IUPHAR/BPS Guide to PHARMACOLOGY, Nov. 13, 2014, 6 pages.

"Pidilizumab Report", IUPHAR/BPS Guide lo PHARMACOLOGY, Mar. 26, 2020, 2 pages.

"Sec submission from Medivation", U.S. Securities and Exchange Commission, Form 8-K, Medivation, Inc., Jan. 25, 2016, 4 pages.

Stenner et al. (2018) "Cancer Immunotherapy and the Immune Response in Follicular Lymphoma", Frontiers in Oncology, 8(219):1-7.

Vonderhelde et al. (2013) "Agonistic CD40 antibodies and cancer therapy", Clin. Cancer Res., 19(5):1035-1043.

Drew M. Pardoll (2012) "The blockade of immune checkpoints in cancer immunotherapy", Nature, 12:252-264.

Capece et al. (2012) "Targeting Costimulatory Molecules to Improve Antitumor Immunity", Journal of Biomedicine and Biotechnology, pp. 1-17.

* cited by examiner

IL-15/IL-15RALPHA BASED CONJUGATES PURIFICATION METHOD

This application claims priority to International Application No. PCT/EP2015/000473, filed Mar. 3, 2015, and titled "IL-15/IL-15RALPHA BASED CONJUGATES PURIFICATION METHOD", which in turn claims the priority of European patent application No. EP 14000742.8 filed on Mar. 3, 2014, both of which are herein incorporated by reference in their entireties.

FIELD OF THE INVENTION

The present invention relates to the field of biochemical engineering. More particularly, the invention concerns an improved biochemical recovery process in which IL-15/IL-15Ralpha based conjugates can be refolded and recovered in monomeric form. This composition can be used in pharmaceutical formulations.

BACKGROUND

Among immunotherapies, those based on cytokines are of particular interest. These molecules, which are soluble molecules, are regulating the humoral and/or cellular immunity. Among them, IL-2, IL-7, IL-12 and IL-15 are of more particular interest since they are inducing NK cells survival and/or proliferation; thus being interesting as adjuvant for treating infection or cancer.

The cytokine interleukin-15 (IL-15) was originally identified in culture supernatants of the simian kidney epithelial cell line CV-1/EBNA and the T cell leukemia cell line HuT-102. The IL-15 cDNA sequence encodes a 162 amino acid (aa) precursor protein consisting of a long 48-aa peptide leader and a 114-aa mature protein. Although there is no sequence homology with IL-2, analysis of the amino acid sequence predicts that IL-15, like IL-2, is a member of the four a helix bundle cytokine family.

Interleukin-15 is actually considered as a very promising future drug. Nevertheless, because of its short half-life and other parameters, its production in mammalian cell lines is actually performed at low yields.

New conjugates based on interleukin-15 and its receptor IL-15 R alpha or fragments thereof were described in U.S. Pat. No. 8,124,084 B2 and EP 1,934,353 B1.

Now, and even if these conjugates have a much better half-life, their purification was complicated by the formation of dimeric and multimeric complexes. Moreover, due to the high percentages of dimeric and oligomeric aggregates, the corresponding purified composition can not be used as medicament due to their potential involvement in the immunogenicity/allergenicity reactions against the injected biologicals (anti-drug antibodies, ADA).

Thus, there is a need of new purification method so as to obtain a conjugate composition that can be used as a medicament.

SUMMARY OF THE INVENTION

A purification method useful in the preparation of monomeric conjugate is provided. This method provides liquid pharmaceutical compositions comprising such monomeric conjugate. The method includes conditions that probably enhance refolding of the conjugate during the recovery process.

The inventors have now established that a purification process using anion-exchange chromatography followed by a hydrophobic interaction chromatography enables to obtain the conjugate in a monomeric form, whereas a purification using hydrophobic interaction chromatography followed by an anion-exchange chromatography not. Moreover, the inventors have surprisingly established that the loading step of hydrophobic interaction chromatography must be done by mixing the first eluate with the loading buffer directly into a mixing chamber of the said chromatography column. In fact, such loading procedure is the most efficient one enabling the obtaining of high concentration of active fusion protein under monomeric form without its co-precipitation on the chromatographic resin.

In a first aspect, the invention thus relates to a method for preparing a composition comprising monomeric conjugates from a sample, said conjugate comprising:
   a) a polypeptide comprising the amino acid sequence of interleukin 15 or derivatives thereof, and
   b) a polypeptide comprising the amino acid sequence of the sushi domain of IL-15Rα or derivatives thereof;
wherein said method comprises the use of anion-exchange chromatography followed by a hydrophobic interaction chromatography on said sample.

In a second aspect, the present invention relates to a pharmaceutical composition comprising such a monomeric conjugate.

In a third aspect, the present invention relates to the use of such a composition for treating a cancer and/or an infection in a subject.

DETAILED DESCRIPTION

Figure 1:
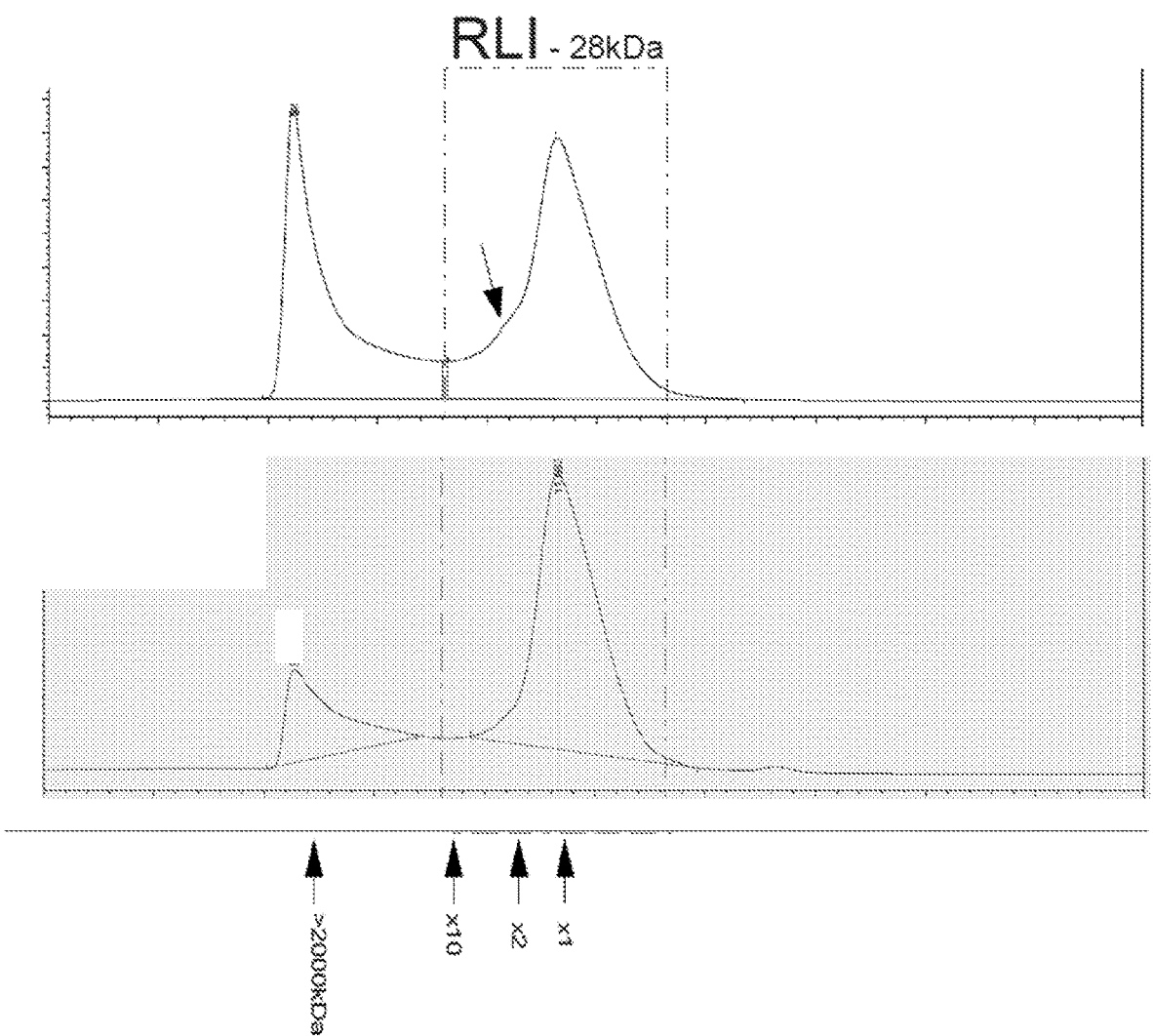
FIG. 1 shows two chromatographic elution profiles of RLI production in CHO cell lines

The present invention is directed to a novel method for preparing a pharmaceutical composition comprising monomeric conjugates.

The term "monomeric" is intended that the majority of conjugate present in the composition is monomeric rather than aggregated. By "aggregated" is intended a physical interaction between the polypeptides molecules that results in multimers—i.e. dimers or oligomers—that remains soluble or that may precipitate out of solution. Most of the time, this aggregated state is irreversible, and results in the denaturation of the conjugate Following its denaturation, it must be noticed that the conjugate may be associated with a strong immunogenicity.

The conjugate percentage (by weight) under monomeric form in that composition will be from at least 80% or greater—i.e. as opposed to its aggregated form-, preferably from at least 90% or more, and more preferably from at least 95%% or more.

The term "sample" refers to a sample of a culture medium of a transformed host cell expressing the conjugate. Host cells used for the invention are mammalian cells, preferably CHO (Chinese Hamster Ovary) cells such as CHO K1 (ATCC number CCL-31, CCL-61 or CRL-9618), CHO-DHFR (ATCC CRL-9096), CHO-DXB-11, CHO cells having the ATCC number ATCC CRL 1610 or CHO DG44; HEK293 (Human Embryonic Kidney) such as 293 (ATCC number CRL-1573) or HEK-293.2sus (ATCC number CRL-1573.3); COS cells such as COS-1 (ATCC number CRL-1650) and COS-7 (ATCC number CRL-1651); PER.C6® cells (human retina derived cell lines; DSM BIOLOGICS, CRUCELL); SP2O such as SP2/0-Ag14 cells (ATCC Accession Number CRL-1851), NSO cells or any cells derived therefrom.

Preferably, said host cell corresponds to CHO cell lines.

In a first preferred embodiment, the method of the invention comprises the steps of:

(a) subjecting the sample to anion-exchange chromatography (AEX) to produce a first eluate;

(b) subjecting the first eluate to hydrophobic interaction chromatography (HIC) to produce a second eluate.

The first step of anion-exchange chromatography (AEX) can be done using AEX column or resin selected from the group comprising or consisting of Q Sepharose, (e.g. Q Sepharose Fast Flow, Q Sepharose XL, Q Sepharose big beads, Q sepharose high performance, Q sepharose XL), DEAE Sephadex A-25, DEAE Sephadex A-50, QAE Sephadex A-25, QAE Sephadex A-50, Sourse 15Q, Sourse 30Q, Resourse Q, Capto Q, Capto DEAE, Mono Q, Toyopearl Super Q, Toyopearl DEAE, Toyopearl QAE, Toyopearl Q, Toyopearl GigaCap Q. TSKgel SuperQ, TSKgel DEAE, Fractogel EMD TMAE, Fractogel EMD TMAE HiCap, Fractogel EMD DEAE, Fractogel EMD DMAE, Macroprep High Q, Macro-prep-DEAE, Unosphere Q, Nuvia Q, POROS HQ, POROS PI, DEAE Ceramic HyperD, and Q Ceramic HyperD. DEAE Sepharose Fast Flow, and ANX Sepharose 4 Fast Flow.

Advantageously, the AEX resin or column corresponds to Q Sepharose or DEAE Sepharose, and more preferably to a strong anion exchanger such as Q Sepharose.

Now, this step a) typically performed in a number of steps comprising equilibration of the column or resin, scouting of the sample, and elution. One or more washing steps may be included after loading and before elution.

Equilibration step is simply performed according to the manufacturer's instruction.

As determined by the inventors, the scouting step is done using a NaCl buffer. As an example, the scouting buffer comprises 0.5 M to 1.5M NaCl, preferably 0.75 M to 1.25 M, and most preferably 1M NaCl.

This scouting step is preferably realized on concentrated and on diafiltrated culture supernatant by using an ultrafiltration cassette.

Anion-exchange chromatography (AEX) manufacturers suggest using a pH of at least one pH unit less than the isoelectric point of the protein to be purified.

Unexpectedly, and whereas RLI1 (SEQ id no 16) or RLI2 (SEQ id no 17) have an electric point of nearly 5.5, the inventors have established that the step a) must be performed at a pH equal or greater than 7.0, and preferably equal or greater than 7.5.

The elution step for the anion-exchange chromatography (AEX), is carried out in a gradient using saline buffer from 1 to 0 M NaCl, and preferably from 0.75 to 0 M NaCl.

The step b) of hydrophobic interaction chromatography (HIC) can be done using HIC column or resin selected from the group comprising or consisting of Phenyl Sepharose, Butyl Sepharose, Octyl Sepharose, ToyoPearl Hexyl-650, ToyoPearl Ether-650, Hydrocell C3, Hydreocell Phenyl 1500, or Hydrocell C4 1500.

Advantageously, the HIC resin or column corresponds to Phenyl Sepharose.

As for the step a), this step b) typically includes a number of steps comprising equilibration of the column or resin, loading of the sample, and elution. One or more washing steps may be included after loading and before elution.

Again, the equilibration step is simply performed according to the manufacturer's instruction.

For the scouting step, the buffer solution contains an ammonium salt such as ammonium sulfate or ammonium acetate, preferably ammonium sulfate. As an example, the scouting buffer comprises 0.75 M to 2.5 M ammonium sulfate, preferably 1 M to 2 M ammonium sulfate, and most preferably 1.5 to 2 M ammonium sulfate.

This scouting step is critical. In the experience realized by the inventors, all the purification results in variable amount of conjugate, which conjugate was mainly under aggregated form.

Unexpectedly, the inventors succeeded in the obtaining of monomeric forms of conjugate by mixing the first eluate obtained from step a) with the scouting buffer directly on said chromatographic column or resin, more especially directly into a mixing chamber of said chromatographic column or resin.

The elution step is carried out in a gradient using saline buffer solution, from 2 to 0 M ammonium sulfate, preferably from 1.5 to 0 M ammonium sulfate.

The method of the invention may comprise one or more further steps.

As an example, the method of the invention may comprise the step of subjecting the second eluate to Size-exclusion chromatography (SEC) to produce a third eluate.

This step of Size-exclusion chromatography (SEC) can be done by using SEC column like Superdex 200 or Superdex 75.

As another example, the method of the invention may also comprise the step of subjecting the second eluate to still another anion-exchange chromatography (AEX) to produce a third eluate.

This step of anion-exchange chromatography can be done as described previously.

In a still preferred embodiment, the method of the invention further comprises the step of using the conjugate obtained for the preparation of a medicament.

The term "conjugate" is used in its general meaning in the art and refers to a covalent or non covalent complex, preferably to a covalent complex and most preferably to a fusion protein.

The term "interleukin 15" in its general meaning in the art and refers to a cytokine with structural similarity to IL-2 (GRABSTEIN et al., *Science*, vol. 264(5161), p:965-968, 1994). This cytokine is also known as IL-15, IL15 or MGC9721. This cytokine and IL-2 share many biological activities and they were found to bind common hematopoietin receptor subunits. Thus, they may compete for the same receptor, negatively regulating each other's activity. It has been established that IL-15 regulates T and natural killer cells activation and proliferation, and that the number of CD8+ memory cells is shown to be controlled by a balance between this cytokine and IL2. IL-15 activity can be measured by determining its proliferation induction on kit225 cell line (HORI et al., *Blood*, vol. 70(4), p:1069-72, 1987), as disclosed in the Examples.

Said IL-15 or derivatives thereof have at least 10% of the activity of human interleukin-15 on the proliferation induction of kit225 cell line, preferably at least 25% and more preferably at least 50%.

Said interleukin 15 is a mammalian interleukin 15, preferably a primate interleukin 15, and more preferably a human interleukin 15.

Mammalian interleukin 15 can be simply identified by the skilled person. As an example, one can cite Interleukin 15 from *Sus scrofa* (Accession number ABF82250), from *Rattus norvegicus* (Accession number NP_037261), from *Mus masculus* (Accession number NP_032383), from *Bos Taurus* (Accession number NP_776515), from *Oryctolagus cuniculus* (Accession number NP_001075685), from *Ovies aries* (Accession number NP 001009734), from *Felis catus* (Accession number NP_001009207), from *Macaca fascicularis* (Accession number BAA19149), from *Homo sapiens* (Accession number NP 000576), from *Macaca Mulatta* (Accession number NP_001038196), from *Cavia porcellus* (Accession number NP_001166300), or from *Chlorocebus sabaeus* (Accession number ACI289).

As used herein, the term "mammalian interleukin 15" refers to the consensus sequence SEQ ID no 1.

Primate interleukin 15 can be simply identified by the skilled person. As an example, one can cite Interleukin 15 from *Sus scrofa* (Accession number ABF82250), from *Oryctolagus cuniculus* (Accession number NP_001075685), from *Macaca fascicularis* (Accession number BAA19149), from *Homo sapiens* (Accession number NP_000576), from *Macaca Mulatta* (Accession number NP_001038196), or from *Chlorocebus sabaeus* (Accession number ACI289).

As used herein, the term "primate interleukin 15" refers to the consensus sequence SEQ ID no2.

Human interleukin 15 can be simply identify by the skilled person and refers to the amino acids sequence SEQ ID no 3.

As used herein, the term "interleukin 15 derivatives" refers to an amino acid sequence having a percentage of identity of at least 92.5% (i.e. corresponding to about 10 amino acids substitutions) with an amino acid sequence selected in the group consisting of SEQ ID no : 1, SEQ ID no 2and SEQ ID no 3, preferably of at least 96% (i.e. corresponding to about 5 amino acids substitutions), and more preferably of at least 98.5% (i.e. corresponding to about 2 amino acids substitutions) or of at least 99% i.e. corresponding to about 1 amino acid substitution). Such derivatives can be simply identified by the skilled person in view of its personal knowledge and of the teaching of the present patent application. As an example of such derivatives, one can cite those described in the International Patent Application PCT WO 2009/135031. It will also be understood that natural amino acids may be replaced by chemically modified amino acids. Typically, such chemically modified amino acids increase the polypeptide half life.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compare the local regions of similarity. The best sequences alignment to perform comparison can be realized, beside by a manual way, by using the global homology algorithm developed by SMITH and WATERMAN (*Ad. App. Math.*, vol. 2, p:482, 1981), by using the local homology algorithm developed by NEDDLEMAN and WUNSCH (*J. Mol. Biol.*, vol. 48, p:443, 1970), by using the method of similarities developed by PEARSON and LIPMAN (*Proc. Natl. Acd. Sci. USA*, vol. 85, p:2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., *Nucleic Acids Research*, vol. 32, p:1792, 2004). To get the best local alignment, one can preferably use the BLAST software with the BLOSUM 62 matrix. The identity percentage between two sequences of amino acids is determined by comparing these two sequences optimally aligned, the amino acids sequences being able to encompass additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

Preferably, the interleukin 15 derivatives are IL-15 agonist or superagonist. One skilled in the art can simply identify an IL-15-agonist or -superagonist. As a example of IL-15-agonist or -superagonist, one can cite the ones disclosed in the International patent application WO 2005/085282 or in ZHU et al. (*J. Immunol.*, vol. 183 (6), p:3598-607, 2009).

Still preferably, said IL-15 agonist or superagonist is selected in the group comprising/consisting of L45D, L45E, S51D, L52D, N72D, N72E, N72A, N72S, N72Y and N72P (in reference to sequence of human IL-15, SEQ ID no 3).

As used herein the term "the sushi domain of IL-15Rα" has its general meaning in the art and refers to a domain beginning at the first cysteine residue (C1) after the signal peptide of IL-15Rα, and ending at the fourth cysteine residue (C4) after said signal peptide. Said sushi domain corresponding to a portion of the extracellular region of IL-15Rα is necessary for its binding to IL-15 (WEI et al., *J. Immunol.*, vol. 167(1), p:277-282, 2001).

Said sushi domain of IL-15Rα or derivatives thereof has at least 10% of the binding activity of the sushi domain of human IL-15Rα to human interleukin-15, preferably at least 25% and more preferably at least 50%. Said binding activity can be simply determined by the method disclosed in WEI et al. (abovementioned, 2001).

Said sushi domain of the IL-15Rα is the sushi domain of a mammalian IL-15Rα, preferably the sushi domain of a primate IL-15Rα and more preferably the sushi domain of the human IL-15Rα.

The sushi domain of a mammalian IL-15Rα can be simply identified by the skilled person. As an example, one can cite the sushi domain of a IL-15Rα from *Rattus norvegicus* (Accession number XP_002728555), from *Mus masculus* (Accession number EDL08026), from *Bos Taurus*

(Accession number XP_002692113), from *Oryctolagus cuniculus* (Accession number XP_002723298), from *Macaca fascicularis* (Accession number ACI42785), from *Macaca nemestrina* (Accession number ACI42783), from *Homo sapiens* (Accession number CAI41081), from *Macaca Mulatta* (Accession number NP_001166315), *Pongo abelii* (Accession number XP_002820541), *Cercocebus torquatus* (Accession number AC142784), *Callithrix jacchus* (Accession number XP_002750073), or from *Cavia porcellus* (Accession number NP_001166314).

As used herein, the term "sushi domain of a mammalian IL-15Rα" refers to the consensus sequence SEQ ID no4.

Preferably, the polypeptide comprising the amino acid sequence of the sushi domain of a mammalian IL-15Rα refers to the consensus sequence SEQ ID no5.

The sushi domain of a primate IL-15Rα can be simply identified by the skilled person. As an example, one can cite sushi domains of IL-15Rα from *Oryctolagus cuniculus*, from *Macaca fascicularis*, from *Macaca nemestrina*, from *Homo sapiens*, from *Macaca Mulatta, Pongo abelii, Cercocebus torquatus*, or *Callithrix jacchus*.

As used herein, the term "sushi domain of a primate IL-15Rα" refers to the consensus sequence SEQ ID no6.

Preferably, the polypeptide comprising the amino acid sequence of the sushi domain of a primate IL-15Rα refers to the consensus sequence SEQ ID no7.

The sushi domain of human IL-15Rα can be simply identified by the skilled person and refers to the amino acids sequence SEQ ID no 8.

Preferably, the polypeptide comprising the amino acid sequence of the sushi domain of human IL-15Rα refers to SEQ ID no 9.

As used herein, the term "derivatives of the sushi domain of the IL-15Rα" refers to an amino acid sequence having a percentage of identity of at least 92% (i.e. corresponding to about 5 amino acids substitutions) with an amino acid sequence selected in the group consisting of SEQ ID no: 4, SEQ ID no5, SEQ ID no6, SEQ ID no: 7, SEQ ID no8, and SEQ ID no9, preferably of at least 96% (i.e. corresponding to about 2 amino acids substitutions), and more preferably of at least 98% (i.e. corresponding to about 1 amino acids substitutions). Such derivatives comprise the four cysteine residues of the sushi domain of L-15Rα and can be simply identified by the skilled person in view of his/her general knowledge and of the teaching of the present patent application. It will also be understood that natural amino acids may be replaced by chemically modified amino acids. Typically, such chemically modified amino acids enable to increase the polypeptide half life.

According to a preferred embodiment, the conjugate comprises (ii) a polypeptide comprising the amino acid sequence of the sushi and hinge domains of IL-15Rα or derivatives thereof.

The IL-15Rα hinge domain is defined as the amino acid sequence that begins at the first amino residue after the sushi domain and that ends at the last amino acid residue before the first potential site of glycosylation. In human IL-15Rα, the amino acid sequence of the hinge region consists of the fourteen amino acids which are located after the sushi domain of this IL-15Ralpha, in a C-terminal position relative to said sushi domain, i.e., said IL-15Ralpha hinge region begins at the first amino acid after said (C4) cysteine residue, and ends at the fourteenth amino acid (counting in the standard "from N-terminal to C-terminal" orientation).

Said sushi and hinge domains of IL-15Rα are the sushi and hinge domains of a mammalian IL-15Rα, preferably the sushi and hinge domains of a primate IL-15Rα and more preferably the sushi and hinge domains of the human IL-15Rα.

The amino acid sequence of the sushi and hinge domains of a mammalian IL-15Rα can be simply identified by the skilled person. As used herein, the term "sushi and hinge domains of a mammalian IL-15Rα" refers to the consensus sequence SEQ ID no10.

The amino acid sequence of the sushi and hinge domains of a primate IL-15Rα can be simply identified by the skilled person. As used herein, the term "sushi and hinge domains of a primate IL-15Rα" refers to the consensus sequence SEQ ID no11.

The amino acid sequence of the sushi and hinge domains of human IL-15Rα can be simply identified by the skilled person. As used herein, the term "sushi and hinge domains of human IL-15Rα" refers to the consensus sequence SEQ ID no12.

As used herein, the term "derivatives of the sushi and hinge domains of IL-15Rα" refers to an amino acid sequence having a percentage of identity of at least 93% (i.e. corresponding to about 5 amino acids substitutions) with an amino acid sequence selected in the group consisting of SEQ ID no: 10, SEQ ID no11, and SEQ ID no12, preferably of at least 97% (i.e. corresponding to about 2 amino acids substitutions), and more preferably of at least 98% (i.e. corresponding to about 1 amino acids substitution). Such derivatives comprise the four cysteine residues of the sushi domain of L-15Rα and can be simply identified by the skilled person in view of its general knowledge and of the teaching of the present patent application. It will also be understood that natural amino acids may be replaced by chemically modified amino acids. Typically, such chemically modified amino acids enable to increase the polypeptide half-life.

Both polypeptides a) and b) of the conjugate may be linked non-covalently such as in the complex disclosed in U.S. Pat. No. 8,124,084 B2. Said conjugate or complex can be simply obtained by providing a suitable amount of the polypeptide a), providing a suitable amount of the polypeptide b), admixing both polypeptides under suitable pH and ionic conditions for a duration sufficient to allow complex (i.e. conjugate) formation, and optionally concentrating or purifying said complex. The polypeptides of the complex (i.e. conjugate) can be formed, for example, using a peptide synthesizer according to standard methods; by expressing each polypeptide separately in a cell or cell extract, then isolating and purifying the polypeptide. Optionally, the therapeutic polypeptide complex of the invention can be formed by expressing both polypeptides i) and ii) in the same cell or cell extract, then isolating and purifying the complexes, for example, using chromatographic techniques, such as affinity chromatography with antibodies to the lymphokine portion, the lymphokine receptor portion, or to the complex.

Both polypeptides a) and b) of the conjugate may be also covalently linked using bifunctional protein coupling agents or in a fusion protein.

The polypeptides a) and b) of the conjugate may be glycosylated or unglycosylated. In fact, the inventors have established that both glycosylated or unglycosylated RLI have the same specific activity in vitro. Now, the polypeptides a) and b) of the conjugate are preferably glycosylated.

Bifunctional protein coupling agents are well known from the skilled person such as methods using them, and include, as examples, N-succinimidyl (2-pyridyldithio) propionate (SPDP), succinimidyl (N-maleimidomethyl) cyclohexane-1-carboxylate, iminothiolane (IT), bifunctional derivatives of imidoesters (such as dimethyl adipimidateHCL), active esters (such as disuccinimidylsuberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene).

The term "fusion protein" refers to a protein created through the joining of two or more genes which originally coded for separate proteins. It is also known as a chimeric protein. Translation of this fusion gene results in a single polypeptide with functional properties deriving from each of the original proteins. Recombinant fusion proteins are created artificially by recombinant DNA technology for use in biological research or therapeutics. A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

In a preferred embodiment, the conjugate is a fusion protein.

The amino acid sequence of interleukin 15 or derivatives thereof can be in a C-terminal or in an N-terminal position relative to the amino acid sequence of the sushi domain of IL-15Rα or derivatives thereof. Preferably, the amino acid sequence of the interleukin 15 or derivatives thereof is in a C-terminal position relative to the amino acid sequence of the sushi domain of IL-15Rα or derivatives thereof.

The amino acid sequence of interleukin 15 or derivatives thereof and the amino acid sequence of the sushi domain of IL-15Rα or derivatives thereof may be separated by a "linker" amino acid sequence. Said "linker" amino acid sequence may be of a length sufficient to ensure that the fusion protein form proper secondary and tertiary structures.

The length of the linker amino acid sequence may vary without significantly affecting the biological activity of the fusion protein. Typically, the linker amino acid sequence comprises at least one, but less than 30 amino acids e.g., a linker of 5-30 amino acids, preferably of 10-30 amino acids, more preferably of 15-30 amino acids, still more preferably of 15-25 amino acids, most preferably of 18-22 amino acids.

Preferred linker amino acid sequences are those which allow the conjugate to adopt a proper conformation (i.e., a conformation allowing a proper signal transducing activity through the IL-15Rbeta/gamma signaling pathway).

The most suitable linker amino acid sequences (1) will adopt a flexible extended conformation, (2) will not exhibit a propensity for developing ordered secondary structure which could interact with the functional domains of fusion proteins, and (3) will have minimal hydrophobic or charged character which could promote interaction with the functional protein domains.

Preferably, the linker amino acid sequence comprises near neutral amino acids selected in the group comprising Gly (G), Asn (N), Ser (S), Thr (T), Ala (A), Leu (L), and Gln (Q), most preferably in the group comprising Gly (G), Asn (N), and Ser (S).

Examples of linker sequences are described in U.S. Pat. Nos. 5,073,627 and 5,108,910.

Illustrative flexible linkers that are more particularly suitable for the present invention include those coded by the sequences of SEQ ID no13 (SGGSGGGGSGGGSGGGG-SLQ), SEQ ID no14 (SGGSGGGGSGGGSGGGGSGG) or SEQ ID no15 (SGGGSGGGGSGGGGSGGGSLQ).

Still preferably, the conjugate is a fusion protein having the sequence SEQ ID no16 or SEQ ID no17.

In a second aspect, the invention relates to a pharmaceutical composition comprising such a monomeric conjugate, eventually associated with a pharmaceutically acceptable carrier.

The expression "pharmaceutically acceptable" refers to molecular entities and compositions that are physiologically tolerable and do not typically produce allergic or similar undesirable reactions, such as gastric upset, dizziness and the like when administered to a human. Preferably, as used herein, the expression "pharmaceutically acceptable" means approvable by a regulatory agency of the Federal or state government or listed in the U.S. Pharmacopeia or other generally recognized pharmacopeia for use in animals, and more particularly in humans.

The term "carrier" refers to a solvent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like.

The route of administration of the combination of the invention is preferably parenteral; as used herein, the term "parenteral" includes intravenous, intramuscular, subcutaneous, rectal, vaginal or intraperitoneal administration. Thus, the pharmaceutical composition contains vehicles which are pharmaceutically acceptable for a formulation intended to be injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Suitable pharmaceutical carriers are described in "Remington's Pharmaceutical Sciences" by E. W. Martin.

Of these, intravenous administration is most preferred.

The conjugate may be solubilized in a buffer or water or incorporated in emulsions, microemulsions, hydrogels (e.g. PLGA-PEG-PLGA triblock copolymers-based hydrogels), in microspheres, in nanospheres, in microparticles, in nanoparticles (e.g. poly(lactic-co-glycolic acid) microparticles (e.g. poly lactic acid (PLA); poly (lactide-co-glycolic acid) (PLGA); polyglutamate microspheres, nanospheres, microparticles or nanoparticles), in liposomes, or other galenic formulations. In all cases, the formulation must be sterile and fluid to the extent of acceptable syringability. It must be stable under the conditions of manufacture and storage and must be preserved against the contaminating action of microorganisms, such as bacteria and fungi.

Dispersions can also be prepared in glycerol, liquid polyethylene glycols, mixtures thereof and in oils. Under ordinary conditions of storage and use, these preparations contain a preservative to prevent the growth of microorganisms.

The conjugate can be formulated into a composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or a dispersion medium containing, for example, water, ethanol, polyol (for example, glycerol, propylene glycol, and liquid polyethylene glycol, and the like), suitable mixtures thereof, and vegetables oils. The conjugates of the invention may also be modified, by pegylation as an example, so as to increase its biodisponibility.

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate, gelatin, polyols, half-life enhancing covalent and non covalent formulations.

There are numerous causes of peptide instability or degradation, including hydrolysis and denaturation. Hydrophobic interaction may cause clumping of molecules together (i.e. aggregation). Stabilizers may be added to reduce or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from ionic and non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (E.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycerol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

In a third aspect, the present invention relates to the use of such a pharmaceutical composition for treating a cancer, an infection, and/or an immunodeficiency disorder in a subject.

As used herein, the term "subject" denotes a mammal, such as a rodent, a feline, a canine or a primate, and most preferably a human.

In the context of the invention, the term "treating", as used herein, means reversing, alleviating, inhibiting the progress of, or preventing the disorder or condition to which such term applies, or one or more symptoms of such disorder or condition.

The term "treating cancer" as used herein means the inhibition of the growth of cancer cells. Preferably such treatment also leads to the regression of tumor growth, i.e., the decrease in size of a measurable tumor. Most preferably, such treatment leads to the complete regression of the tumor.

The term "treating an infection" as used herein means the inhibition of microbes' replication/proliferation.

The term "treating an immunodeficiency disorder" as used herein means the induction of NK cells and/or T cells.

An "effective amount" of the conjugate is an amount which is sufficient to induce the regression of tumor growth or of microbes' replication. The doses used for the administration can be adapted as a function of various parameters, in particular as a function of the mode of administration used, of the relevant pathology, or alternatively of the desired duration of treatment. Naturally, the form of the pharmaceutical composition, the route of administration, the dosage and the regimen naturally depend on the condition to be treated, the severity of the illness, the age, weight, and sex of the subject, etc. The ranges of effective doses provided below are not intended to limit the invention and represent preferred dose ranges. However, the preferred dose can be tailored to the individual subject, as is understood and determinable by one of skill in the art, without undue experimentation.

In the following, the invention is described in more detail with reference to amino acid sequences, nucleic acid sequences and examples. However, no limitation of the invention is intended by the details of the examples. Rather, the invention pertains to any embodiment which comprises details which are not explicitly mentioned in the examples herein, but which the skilled person finds without undue effort.

EXAMPLES

1) Analysis of RLI Production Profile

The nucleotide sequence coding for RLI1 and RLI2 (SEQ ID no16 and SEQ ID no17) were cloned in pcDNA3.1 plasmids by GENEART. A 40 kDa linear PEI was obtained from POLYSCIENCE. A 1 mg/mL stock solution was prepared by dissolving the PEI in water with heating, neutralizing by NaOH, and sterilizing by filtration through a 0.22 µm filter. The solution stock was aliquoted and stored at −20° C. Plasmids DNA for transfections were purified using the plasmid purification kits following the manufacturer's protocol (MACHEREY-NAGEL) and sterilizing by filtration through a 0.22 µm filter.

Routinely maintained CHO-S(INVITROGEN) cells were seeded at a density of $1 \times 10^6$ cells/mL in PowerCHO2 Medium (LONZA), and cultured overnight at 37° C. in a shaking incubator (100 rpm) with 5% $CO_2$. For transfection, cells were then diluted in CD-CHO medium (INVITROGEN) to $2 \times 10^6$ cells/mL The transfection complexes were prepared in 10% of the culture volume using NaCl 150 mM. Expression constructs DNA (2.5 mg/L of culture volume) were mixed with PEI diluted in NaCl (10 mg/L of final culture volume) and incubated for 10 min at room temperature before adding to the culture. Cells were cultured in a shaking incubator (130 rpm) at 37° C. for 5 h before doubling the culture volume with PowerCHO2 medium. Supernatants were collected 5 days post-transfection.

Collected supernatant were centrifuged at 3000 rpm for 20 minutes at 4° C., equilibrated at pH 7.8 with NaOH and filtered through a 0.22 µm filter before analysis. The RLI expression pattern was analyzed using SUPERDEX 200 5/150 GL according to the manufacturer's instruction. For this analysis, diluted (0.15 mg/mL) and not diluted samples were used. The flow rate was 0.2 mL/min and the running buffer PBS. The protein elution was monitored by absorbance at 215 nm.

The results for different purification are shown in table I and in FIG. 1.

TABLE I

| Batch | Soluble aggregates | Peaks number | Oligomer aggregates | Monomer | Size monomer (kDa) |
|---|---|---|---|---|---|
| 1 | Yes | 2(+) | 48% | 52% | 27.64 |
| 2 | Yes | 2 | 43% | 57% | 26.28 |

The results show the existence of two distinctive peaks on the chromatogram. The first peak corresponds to aggregates whose size is higher than 2000 kDa. The second peak corresponds to the monomer of RLI. Now, this second peak sometimes contains a shoulder (indicated by an arrow) which could represent a dimer of RLI.

Thus, the RLI production contains a mere proportion of aggregates. This conclusion is not surprising since IL15 alone is already known to aggregate at low level in the cultivation supernatant. Now, such aggregation is problematic since the obtained composition can not be used as pharmaceutical composition.

According to the literature, the causes of aggregation can be multiple. Such an aggregation can occur from cell culture process up to final filling operation. This aggregation may be the results of medium components (because of host cell proteins, RLI concentration or dissolved oxygen), of the purification process (because of the purification technique (HIC, AEX, Affinity . . . ), of the elution conditions (pH, ionic strength, protein concentration . . . ), of the ultrafiltration/diafiltration process (Shear stress, surface concentration), or of the formulation (because of the Buffer (pH, ionic strength, excipient . . . ). Because of this multiparameters equation, the identification of the aggregation cause during the overall process is a very challenging work, which work is not always successful.

2) Analysis by Fractionation

In order to determine the chromatographic behavior of the purified components and to analyze the content of each elution peak, a sample of a previously purified protein was analyzed using SUPERDEX 75 10/300 GL according to the manufacturer's instruction. For this analysis, a 50 µl sample was used. The flow rate was 1 mL/min and the running buffer was PBS. The protein elution was monitored by absorbance at 215 nm.

Figure 2:
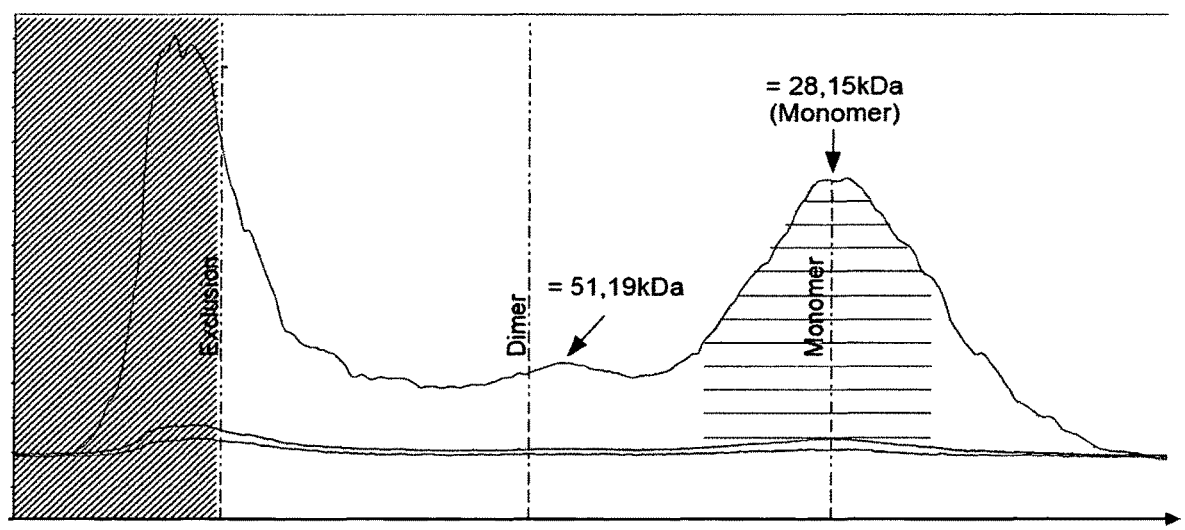
FIG. 2 shows a size exclusion chromatography profile of an RLI production in CHO cell lines
Figure 3:
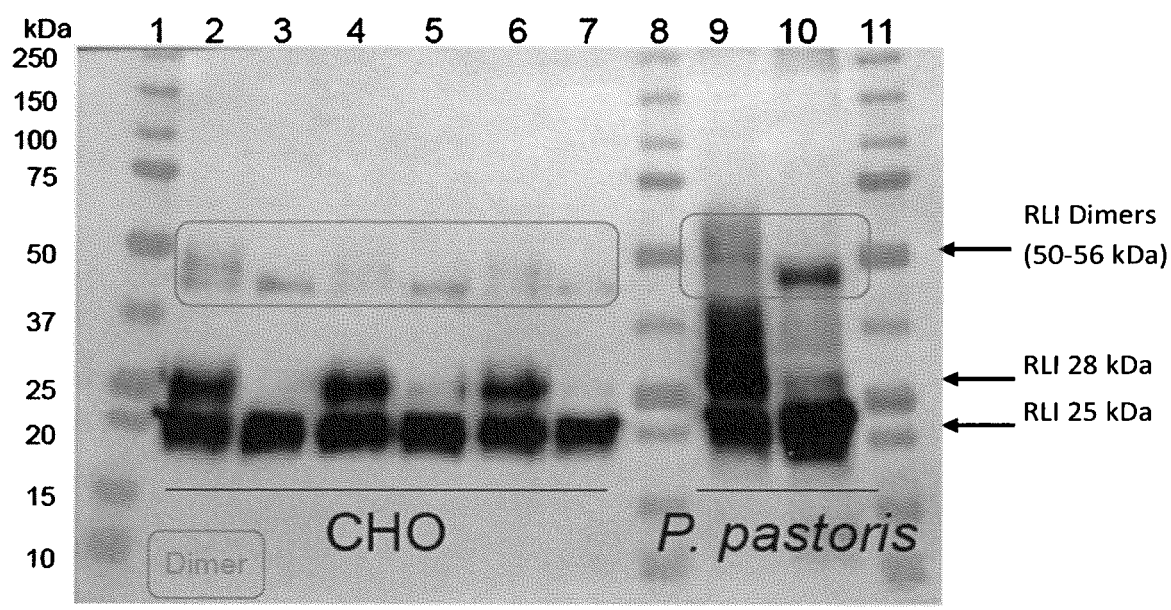
FIG. 3 shows a western blot using IL-15 antibody on RLI produced in CHO cell lines (lanes 2 to 7) or in *Pichia pastoris* (lanes 9 and 10). Deglycosylation of RLI by PNGase correspond to lanes 3, 5, 7 and 10.

The SEC (Size Exclusion Chromatography) chromatogram is shown in FIG. 2, the Western Blot analysis of some elution fractions is shown in FIG. 3 and the results for this purification is summarized in table II.

TABLE II

| Batch | Soluble aggregates | Peaks number | Oligomer aggregates | Monomer | Size monomer (kDa) |
|---|---|---|---|---|---|
| 3 | Yes | 3(+) | 49% | 51% | 28.12 |

The results confirm the existence of a first peak corresponding to the exclusion limit of the column (FIG. 2). This peak comprises the soluble aggregates (>110 kDa) of the RLI protein, which aggregates comprise both glycosylated and unglycosylated RLI proteins (FIG. 3). The second peak corresponds to a RLI dimer and the third to a 28.5 kDa globular protein corresponding to RLI monomer (FIG. 2). The capillary electrophoresis has shown that this third peak comprises both glycosylated and unglycosylated forms but with a slightly offset elution (FIG. 3). As a control, protein purified from *Pichia pastoris* was used. As expected, the glycosylated form is eluted before the non glycosylated one.

Finally, the species distribution is consistent with the previous analysis with 49% of oligomers and/or aggregates and 51% of monomers.

It has been noticed that the storage temperature—i.e. 4° C. or −80° C.—does not influence the RLI oligomerization state. Moreover, these results have shown that RLI is very stable when stored at 4° C. and also after 6 cycles of freeze/thawing at −80° C.

So as to better characterize the aggregation state of RLI products, SEC-MALLS (Size exclusion chromatography coupled to Multi Angle laser Light Scattering). This method allows the determining of the distribution in size of the different multimeric species contained in the protein sample. With this method, the different species are first separated and diluted by SEC and then analyzed by MALLS.

For this analysis, samples of about 35 µg of proteins were used. The flow rate was 0.35 mL/min at 20° C. with a SEC Buffer (4.3 mM $Na_2HPO_4$, 1.4 mM $KH_2PO_4$, 2.7 mM KCl, 137 mM NaCl) on a SHODEX (kW402.5-4F) according to the manufacturer's instruction. INFINITY 1260 chromatography system was used as HPLC detector, DAW-HELEOS 8+(WYATT TECHNOLOGIES) was used as MALLS detector and OPTILAB-rEX was used.

Figure 4:
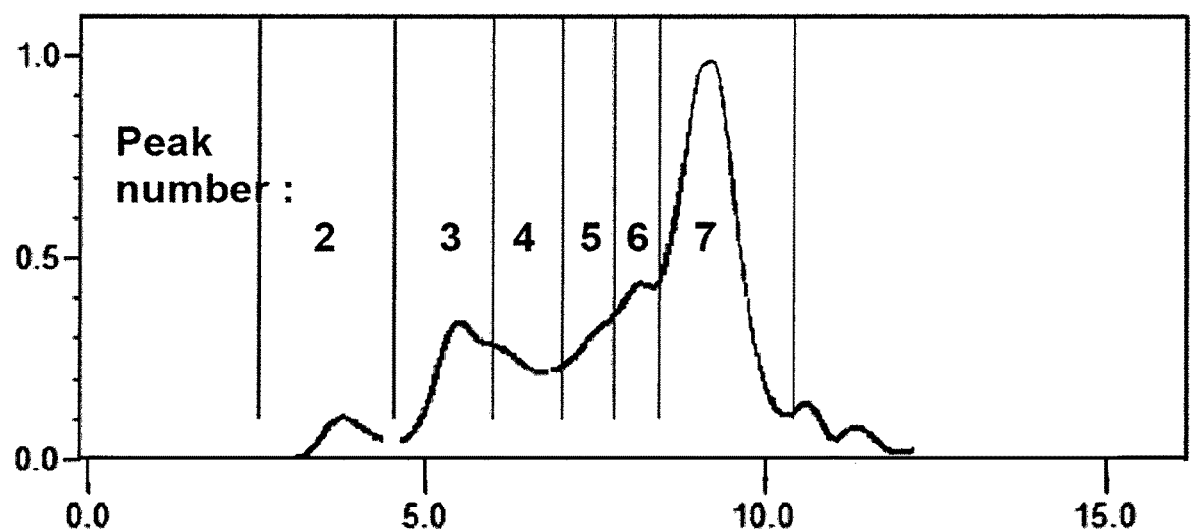
FIG. 4 shows a SEC-MALLS chromatogram for a RLI product (for light scattering)

The FIG. 4 shows an example of a SEC-MALLS chromatogram for a RLI product (for light scattering).

The table III discloses the distribution of the different protein peaks for two RLI batch at room temperature and following three hours incubation.

TABLE III

| Batch | Time after thawing | Aggregates 1 (%) | Aggregates 2 (%) | Octamers (%) | Tetramers (%) | Dimers (%) | Monomers (%) |
|---|---|---|---|---|---|---|---|
| 4 | 0 h | 74.2 | 0.0 | 0.0 | 3.8 | 6.5 | 15.5 |
|   | 3 h | 74.4 | 0.0 | 0.0 | 3.7 | 6.5 | 15.4 |
| 5 | 0 h | 31.3 | 0.0 | 0.0 | 6.5 | 11.5 | 50.6 |
|   | 3 h | 31.7 | 0.0 | 0.0 | 6.9 | 10.5 | 50.7 |

The results have established the existence of six proteins peaks with some minors one corresponding to different forms of RLI in most of the samples. Now, these peaks show no significant evolution in their distribution after 3 hours incubation at room temperature.

These results confirm the existence of multimeric forms in connection with the monomeric one.

3) First Purification Step

This first purification step was developed for the RLI production in *Pichia pastoris*. In a first clarification step, different supernatants obtained from by RLI production in CHO cell were filtrate with a 0.22 µm membrane (cellulose). These supernatants were then diafiltrated with Tris HCl pH 7.5. Ammonium sulphate (AS=$(NH_4)_2SO_4$) was then dissolved in the diafiltrated supernatants so as to obtain an AS final concentration of 1.5M corresponding to the binding buffer. The hydrophobic interaction chromatography columns (Phenyl Sepharose FF) were then scouted with the obtained binding buffers.

The elution was then performed according to manufacturer's instruction.

As compared with the *Pichia pastoris* production, this first purification step results in very low yield and bad reproducibility.

Because of an incorrect experiment, an anion exchange chromatography (AEX) was used for the first step. Surprisingly, the inventors observed that this specific chromatography enables to obtain very good yield. It has resulted from further experiments that this very good yield was observed with very good reproducibility.

Comparative experiments between DEAE-Sepharose and Q-Sepharose have shown that the best yields were obtained with Q Sepharose and that the optimal buffer for scouting on Q- or DEAE-Sepharose was 20 mM Tris HCl, pH 7.5; 1 M NaCl. Whereas manufacturer's instruction suggests the use of a scouting buffer whose pH is at least one unit less than the pI of the protein to purify, the results have shown unexpectedly that the best scouting is obtained at a pH equal or greater than 7.5 (Tris HCl buffer), which pH is nearly two units more than the RLI protein. Now, a lower pH results in very poor scouting and thus poor yield and reproducibility for RLI protein purification.

Moreover, is seems that the DNA of the HO cells binds to RLI and the eluate obtained after this first purification step is contaminated by this DNA.

4) Second Purification Step

So as to obtain a nucleic acid- and of endotoxin-free composition, the inventors have initiated a second round purification.

The best results were obtained with hydrophobic interaction chromatography columns (Phenyl Sepharose Butyl Sepharose, Octyl Sepharose) with 20 mM Tris HCl pH7.5-2 M ammonium sulfate (AS=$(NH_4)_2SO_4$).

Now, and as for the experiences for the first step purification, these experiences enable to obtain RLI protein with very poor yield and reproducibility.

Fortuitously, the inventors observed that the more rapidly the mixture—i.e. of the sample with ammonium sulfate—was charged after its obtaining, the better the yield and reproducibility are. It seems that the salt stability window of the protein depends upon many parameters including temperature impacting on the purification process. Consequently, the inventors mix ammonium sulfate—i.e. upon 0.75 M- and the first eluate directly on the hydrophobic interaction chromatography columns for the scouting step.

After the washing and the elution steps using a gradient between buffer solution A2 (20 mM Tris HCl, pH 7.5) and buffer solution B2 (20 mM Tris HCl, 2 M ammonium sulfate, pH 7.5), the RLI protein was obtained with a very good yield and reproducibility at 37.5% of the gradient. The glycosylated form is eluted slightly later than the unglycosylated form, and partially overlapped the elution window of the unglycosylated form. At the end, the sample was concentrate up to 0.5 to 1 mg/l on an ultrafiltration cassette with a MWCO 5 kDa, and diafiltrated against PBS buffer.

Finally, the results obtained with the inventors' purification process have shown that the RLI protein was obtain with a purity of more than 98%, without no detectable endotoxin, heat choc proteins or residual DNA. Moreover, the analysis of the obtained composition has shown that more than 90% of the RLI protein is under monomeric form satisfying its use in a pharmaceutical composition.

5) Proliferation Activity of the Obtained Pharmaceutical Composition

In order to test the interleukin-15 proliferation activity of the purified proteins, the proliferative responses of Kit 225 and 32Dβ cells to ICK to said proteins were measured by [$^3$H] thymidine incorporation.

Cells were maintained in culture medium for 3 days, washed twice, and starved in medium without cytokine for 24 h or 4 h for Kit 225 and 32Dβ, respectively. They were then seeded in multiwell plates at $10^4$ cells/well in 100 µl, and cultured for 48 h in medium supplemented with increasing concentration of several RLI CHO samples. Human rIL-15 and RLI from baculovirus and from *Pichia pastoris* were used as control.

Cells were pulsed for 16 h with 0.5 µCi/well of [$^3$H] thymidine, harvested onto glass fiber filters, and cell-associated radioactivity was measured.

Figure 5:
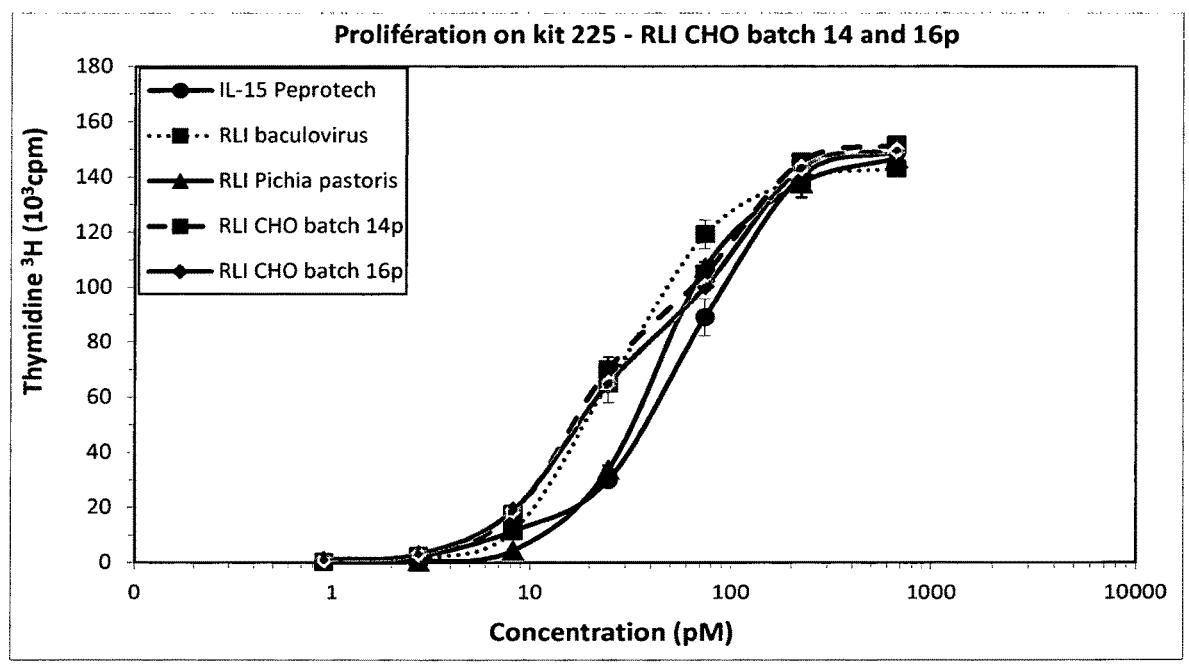
FIG. 5 shows the proliferation activity of different RLI production on kit225 cell lines.
Figure 6:
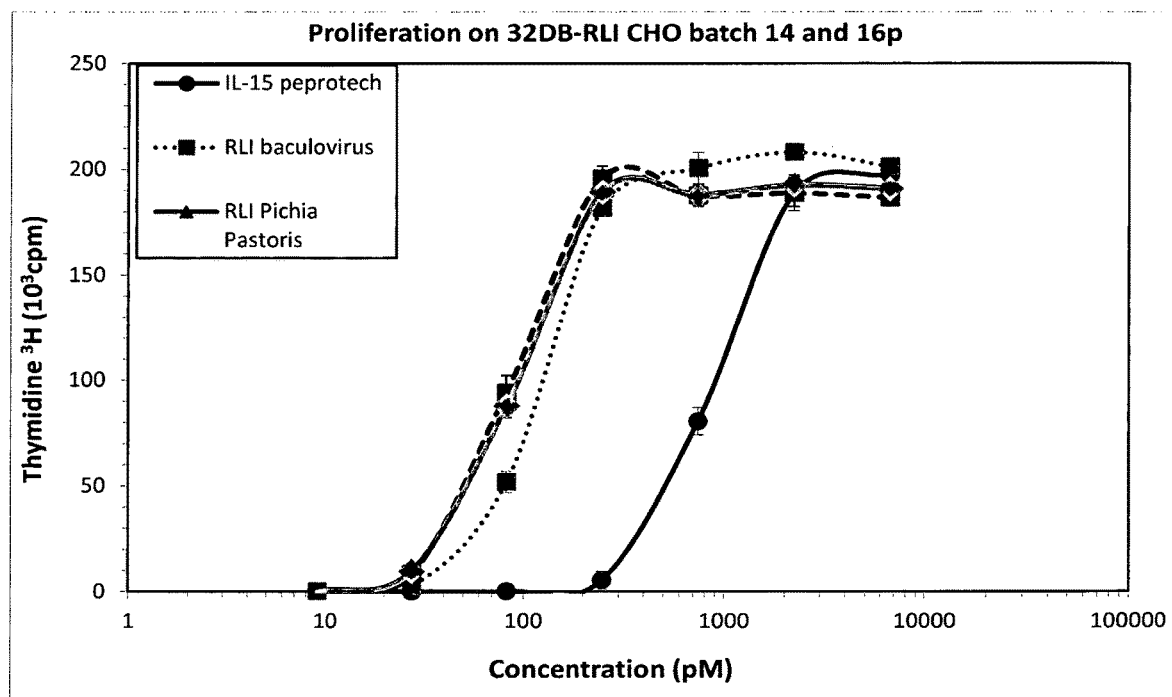
FIG. 6 shows the proliferation activity of different RLI production on 32DB cell lines.

The FIGS. 5 and 6 shows [$^3$H]Thymidine incorporation by Kit 225 and 32Dβ cells respectively cultured with increasing concentrations of rIL-15, of RLI from baculovirus, of RLI from *Pichia pastoris*, and of RLI purified from several CHO production.

The results show that the biological activity of the RLI protein purified with the purification method of the invention has an activity comparable to partially purified RLI proteins. Consequently, the purification method of the invention does not alter the biological activity of RLI.

6) Bioactivity of the Obtained Pharmaceutical Composition in Mouse In Vivo Model C57BL/6 mice obtained from Harlan Laboratories were injected intraperitonealy (i.p) at day 0 and day 1 with 100 µL of PBS, as a negative control, RLI from baculovirus (2 µg/mouse), of RLI from *Pichia pastoris* (2 µg/mouse), and of RLI purified from CHO production (2 µg/mouse). 5 mice were used per group.

Mice were killed by cervical dislocation and spleens are withdrawn on day 4. Spleen was dissociated in a single-cell suspension on a 100 µm-cell strainer with a back of a syringe. Then, blood cells were lysed using ACK solution (Ammonium-Chloride-Potassium). Splenocytes were washed twice times in a complete medium and viable cells were counted using Kova slides. Two millions of splenocytes were stained with following antibodies: anti-CD3, CD4, CD8, NKp46 and LIVE/DEAD® Fixable Aqua to select viable cells. Then, splenocytes were permeabilized according to the manufacturing protocol (EBIOSCIENCE FOXP3 permeabilization buffers) and stained with anti-FoxP3 and Ki67. Isotype of Ki67 was used to identify positive cells. Stained cells were acquired immediately on a FACSCANTO II flow cytometer and analyses were performed using FLOWJO SOFTWARE (TREE STAR). NK cells are CD3 negative NKp46 positive cells.

Figure 7:
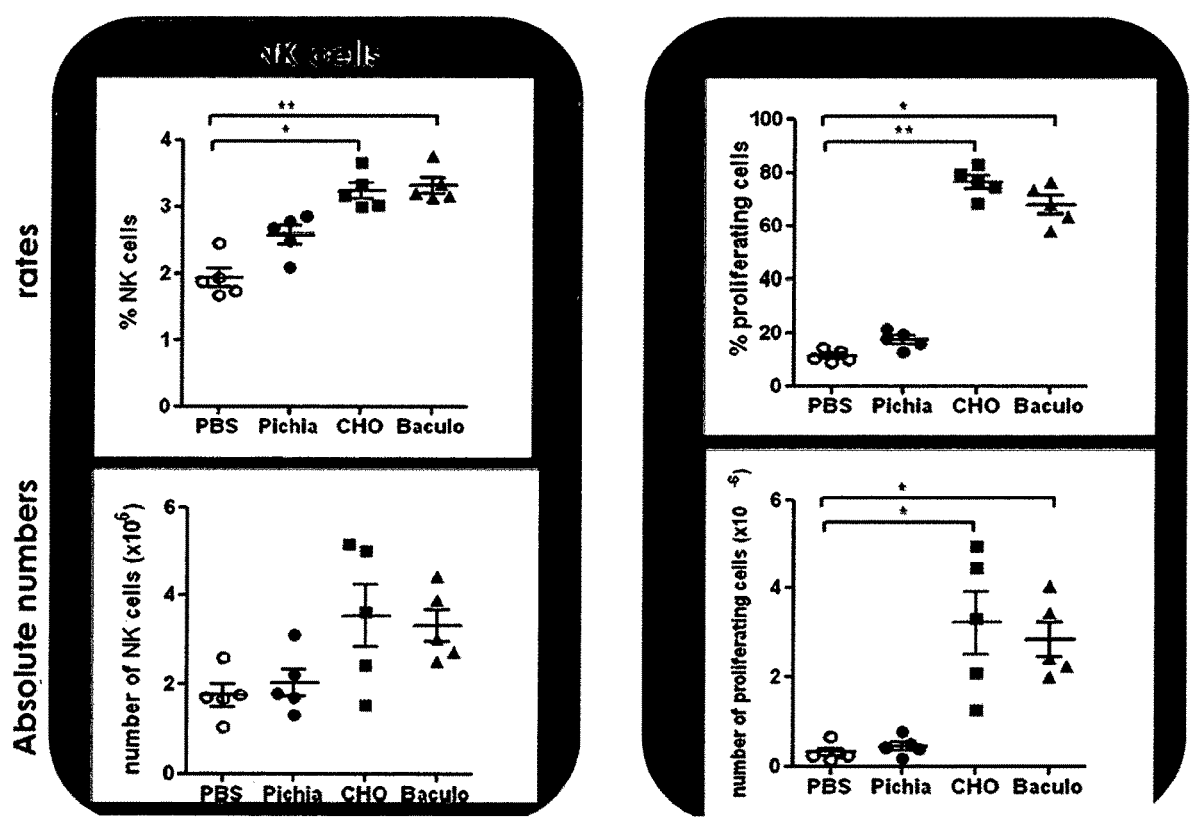
FIG. 7 shows the mice NK proliferation obtained following the mice injection by several RLI samples.

The FIG. 7 represents the proportion of proliferating NK cells, CD8$^+$ T cells, Foxp3$^+$ CD4$^+$ T cells and Foxp3$^-$CD4$^+$ T cells.

The FIG. 7 shows the ratio of NK cells and the absolute number of NK cells for each group.

The FIG. 7 also shows the percentage of proliferative NK cells as compared to total NK cells and the absolute number of proliferative NK cells.

The results show that RLI produced in *Pichia pastoris* has poor in vivo activity as compared to RLI produced in baculovirus. Satisfactorily, the RLI produced in CHO and purified by the method of the invention shows a very good in vivo activity on NK cells.

We claim:

1. A method for preparing a composition comprising monomeric conjugates from a sample, said conjugate consisting of:
   a) a polypeptide consisting of the amino acid sequence of interleukin 15 selected from the sequences set forth in SEQ ID NO: 1 and SEQ ID NO: 3, and
   b) a polypeptide consisting of the amino acid sequence of the sushi domain of IL-15Rα selected from the sequences set forth in set forth in SEQ ID NO: 4, SEQ ID NO: 12, and SEQ ID NO: 8;
   wherein the polypeptides a) and b) of the conjugate are covalently linked in a fusion protein; and wherein the polypeptide a) is in a C-terminal position relative to the amino acid sequence of the of polypeptide b), and polypeptide a) and polypeptide b) are separated by a linker amino acid sequence having a length of 5-30 amino acids, said linker comprising near neutral amino acids selected from the group comprising Gly (G), Asn (N), Ser (S), Thr (T), Ala (A), Leu (L), and Gln (Q); and wherein said method comprises the use of anion-exchange chromatography (AEX) performed at a pH equal or greater to 7.0 followed by a hydrophobic interaction chromatography (HIC), on said sample carried out in a buffer solution containing an ammonium salt.

2. The method of claim 1, wherein said sample corresponds to a sample of a culture medium of a transformed host cell expressing the conjugate, said host cell corresponding to a mammalian cell selected in the group comprising CHO cells, HEK293 cells, COS cells, PER.C6® cells, SP2O cells, NSO cells or any cells derived therefrom, preferably CHO cells.

3. The method of claim 1, wherein said method comprises the steps of:
   a) subjecting the sample to anion-exchange chromatography (AEX) to produce a first eluate; and
   b) subjecting the first eluate to hydrophobic interaction chromatography (HIC) to produce a second eluate.

4. The method of claim 1, wherein the step a) of anion-exchange chromatography (AEX) is done using AEX column or resin selected from the group comprising Q Sepharose, such as Q Sepharose Fast Flow, Q Sepharose XL, Q Sepharose big beads, Q sepharose high performance, Q sepharose XL; DEAE Sephadex A-25, DEAE Sephadex A-50, QAE Sephadex A-25, QAE Sephadex A-50, Sourse 15Q, Sourse 30Q, Resourse Q, Capto Q, Capto DEAE, Mono Q, Toyopearl Super Q, Toyopearl DEAE, Toyopearl QAE, Toyopearl Q, Toyopearl GigaCap Q, TSKgel SuperQ, TSKgel DEAE, Fractogel EMD TMAE, Fractogel EMD TMAE HiCap, Fractogel EMD DEAE, Fractogel EMD DMAE, Macroprep High Q, Macro-prep-DEAE, Unosphere Q, Nuvia Q, POROS HQ, POROS PI, DEAE Ceramic HyperD, Q Ceramic HyperD, DEAE Sepharose Fast Flow, and ANX Sepharose 4 Fast Flow.

5. The method of claim 3, wherein for the step b) of subjecting the sample to hydrophobic interaction chromatography (HIC), the loading step is realized by mixing the first eluate with the loading buffer directly on said chromatography.

6. The method of claim 3 wherein said method further comprised the step of using the conjugate obtained for the preparation of a medicament.

7. The method of claim 1, wherein the polypeptide a) consists of the amino acid sequence of human interleukin 15 set forth in SEQ ID NO: 3, and the polypeptide b) consists of the amino acid sequence of the human sushi domain of IL-15Rα set forth in SEQ ID NO: 8.

8. The method of claim 1, wherein the conjugate is selected from the conjugates set forth in SEQ ID NO: 16 and SEQ ID NO: 17.

9. The method of claim 1, wherein the buffer solution comprises a pH equal or greater to 7.5.

10. The method of claim 1, wherein the buffer solution containing an ammonium salt comprises ammonium sulfate.

* * * * *

```
                              SEQUENCE LISTING

<160> NUMBER OF SEQ ID NOS: 17

<210> SEQ ID NO 1
<211> LENGTH: 114
<212> TYPE: PRT
<213> ORGANISM: artificial sequence
<220> FEATURE:
<223> OTHER INFORMATION: mammalian interleukin 15 consensus sequence
<220> FEATURE:
<221> NAME/KEY: MISC_FEATURE
<222> LOCATION: (1)..(1)
<223> OTHER INFORMATION: X= N, S, T or I
<220> FEATURE:
<221> NAME/KEY: MISC_FEATURE
<222> LOCATION: (3)..(3)
<223> OTHER INFORMATION: X= V, H, I, Q or E
<220> FEATURE:
<221> NAME/KEY: MISC_FEATURE
<222> LOCATION: (4)..(4)
<223> OTHER INFORMATION: X= N, Y, F or D
<220> FEATURE:
<221> NAME/KEY: MISC_FEATURE
<222> LOCATION: (6)..(6)
<223> OTHER INFORMATION: X= I or R
<220> FEATURE:
<221> NAME/KEY: MISC_FEATURE
<222> LOCATION: (7)..(7)
<223> OTHER INFORMATION: X= S, N, L, Y, K or R
<220> FEATURE:
<221> NAME/KEY: MISC_FEATURE
<222> LOCATION: (10)..(10)
<223> OTHER INFORMATION: X= K, E, R or Q
<220> FEATURE:
<221> NAME/KEY: MISC_FEATURE
<222> LOCATION: (11)..(11)
<223> OTHER INFORMATION: X= K, T or R
<220> FEATURE:
<221> NAME/KEY: MISC_FEATURE
<222> LOCATION: (13)..(13)
<223> OTHER INFORMATION: X= E, D or Q
<220> FEATURE:
<221> NAME/KEY: MISC_FEATURE
<222> LOCATION: (14)..(14)
<223> OTHER INFORMATION: X= D, H, S or N
<220> FEATURE:
<221> NAME/KEY: MISC_FEATURE
<222> LOCATION: (16)..(16)
<223> OTHER INFORMATION: X= I or T
<220> FEATURE:
<221> NAME/KEY: MISC_FEATURE
<222> LOCATION: (17)..(17)
<223> OTHER INFORMATION: X=Q, R or K
<220> FEATURE:
<221> NAME/KEY: MISC_FEATURE
<222> LOCATION: (18)..(18)
<223> OTHER INFORMATION: X= S or F
<220> FEATURE:
<221> NAME/KEY: MISC_FEATURE
<222> LOCATION: (19)..(19)
<223> OTHER INFORMATION: X= M, I or L
<220> FEATURE:
<221> NAME/KEY: MISC_FEATURE
<222> LOCATION: (21)..(21)
<223> OTHER INFORMATION: X= I, V or M
<220> FEATURE:
<221> NAME/KEY: MISC_FEATURE
<222> LOCATION: (23)..(23)
<223> OTHER INFORMATION: X=A or T
<220> FEATURE:
<221> NAME/KEY: MISC_FEATURE
<222> LOCATION: (28)..(28)
```

```
<223> OTHER INFORMATION: X=E or D
<220> FEATURE:
<221> NAME/KEY: MISC_FEATURE
<222> LOCATION: (30)..(30)
<223> OTHER INFORMATION: X= D or G
<220> FEATURE:
<221> NAME/KEY: MISC_FEATURE
<222> LOCATION: (31)..(31)
<223> OTHER INFORMATION: X= V, F, A or I
<220> FEATURE:
<221> NAME/KEY: MISC_FEATURE
<222> LOCATION: (34)..(34)
<223> OTHER INFORMATION: X= S, N or R
<220> FEATURE:
<221> NAME/KEY: MISC_FEATURE
<222> LOCATION: (37)..(37)
<223> OTHER INFORMATION: X= V or I
<220> FEATURE:
<221> NAME/KEY: MISC_FEATURE
<222> LOCATION: (39)..(39)
<223> OTHER INFORMATION: X= A or T
<220> FEATURE:
<221> NAME/KEY: MISC_FEATURE
<222> LOCATION: (41)..(41)
<223> OTHER INFORMATION: X= K, Q or N
<220> FEATURE:
<221> NAME/KEY: MISC_FEATURE
<222> LOCATION: (48)..(48)
<223> OTHER INFORMATION: X= Q, G, R, H or E
<220> FEATURE:
<221> NAME/KEY: MISC_FEATURE
<222> LOCATION: (51)..(51)
<223> OTHER INFORMATION: X= S or L
<220> FEATURE:
<221> NAME/KEY: MISC_FEATURE
<222> LOCATION: (52)..(52)
<223> OTHER INFORMATION: X= L, Q or H
<220> FEATURE:
<221> NAME/KEY: MISC_FEATURE
<222> LOCATION: (54)..(54)
<223> OTHER INFORMATION: X= S, F or Y
<220> FEATURE:
<221> NAME/KEY: MISC_FEATURE
<222> LOCATION: (55)..(55)
<223> OTHER INFORMATION: X= G, K, S, N or R
<220> FEATURE:
<221> NAME/KEY: MISC_FEATURE
<222> LOCATION: (56)..(56)
<223> OTHER INFORMATION: X= D, H, S or N
<220> FEATURE:
<221> NAME/KEY: MISC_FEATURE
<222> LOCATION: (57)..(57)
<223> OTHER INFORMATION: X= A, H, M, E, G, S or T
<220> FEATURE:
<221> NAME/KEY: MISC_FEATURE
<222> LOCATION: (58)..(58)
<223> OTHER INFORMATION: X= S, V, P, T, N or D
<220> FEATURE:
<221> NAME/KEY: MISC_FEATURE
<222> LOCATION: (59)..(59)
<223> OTHER INFORMATION: X= I or L
<220> FEATURE:
<221> NAME/KEY: MISC_FEATURE
<222> LOCATION: (60)..(60)
<223> OTHER INFORMATION: X=  H, S, K, N, Y or E
<220> FEATURE:
<221> NAME/KEY: MISC_FEATURE
<222> LOCATION: (61)..(61)
<223> OTHER INFORMATION: X=  D or E
<220> FEATURE:
<221> NAME/KEY: MISC_FEATURE
<222> LOCATION: (62)..(62)
<223> OTHER INFORMATION: X=  T, I or A
<220> FEATURE:
<221> NAME/KEY: MISC_FEATURE
<222> LOCATION: (63)..(63)
<223> OTHER INFORMATION: X=  V or I
<220> FEATURE:
<221> NAME/KEY: MISC_FEATURE
```

```
<222> LOCATION: (64)..(64)
<223> OTHER INFORMATION: X=  E, T, Q, R or K
<220> FEATURE:
<221> NAME/KEY: MISC_FEATURE
<222> LOCATION: (66)..(66)
<223> OTHER INFORMATION: X=  L or V
<220> FEATURE:
<221> NAME/KEY: MISC_FEATURE
<222> LOCATION: (67)..(67)
<223> OTHER INFORMATION: X= I, T or L
<220> FEATURE:
<221> NAME/KEY: MISC_FEATURE
<222> LOCATION: (68)..(68)
<223> OTHER INFORMATION: X=I, M, F, Y or L
<220> FEATURE:
<221> NAME/KEY: MISC_FEATURE
<222> LOCATION: (72)..(72)
<223> OTHER INFORMATION: X= N, T, R, D or S
<220> FEATURE:
<221> NAME/KEY: MISC_FEATURE
<222> LOCATION: (73)..(73)
<223> OTHER INFORMATION: X= S, N, R, T or I
<220> FEATURE:
<221> NAME/KEY: MISC_FEATURE
<222> LOCATION: (75)..(75)
<223> OTHER INFORMATION: X= S or N
<220> FEATURE:
<221> NAME/KEY: MISC_FEATURE
<222> LOCATION: (76)..(76)
<223> OTHER INFORMATION: X= S or A
<220> FEATURE:
<221> NAME/KEY: MISC_FEATURE
<222> LOCATION: (77)..(77)
<223> OTHER INFORMATION: X= N, I or K
<220> FEATURE:
<221> NAME/KEY: MISC_FEATURE
<222> LOCATION: (78)..(78)
<223> OTHER INFORMATION: X= G, E or K
<220> FEATURE:
<221> NAME/KEY: MISC_FEATURE
<222> LOCATION: (79)..(79)
<223> OTHER INFORMATION: X= N, Y, D or T
<220> FEATURE:
<221> NAME/KEY: MISC_FEATURE
<222> LOCATION: (80)..(80)
<223> OTHER INFORMATION: X= V, K or I
<220> FEATURE:
<221> NAME/KEY: MISC_FEATURE
<222> LOCATION: (81)..(81)
<223> OTHER INFORMATION: X= T, A or I
<220> FEATURE:
<221> NAME/KEY: MISC_FEATURE
<222> LOCATION: (83)..(83)
<223> OTHER INFORMATION: X= S, L or T
<220> FEATURE:
<221> NAME/KEY: MISC_FEATURE
<222> LOCATION: (87)..(87)
<223> OTHER INFORMATION: X= E or V
<220> FEATURE:
<221> NAME/KEY: MISC_FEATURE
<222> LOCATION: (93)..(93)
<223> OTHER INFORMATION: X= E or K
<220> FEATURE:
<221> NAME/KEY: MISC_FEATURE
<222> LOCATION: (94)..(94)
<223> OTHER INFORMATION: X= K or R
<220> FEATURE:
<221> NAME/KEY: MISC_FEATURE
<222> LOCATION: (95)..(95)
<223> OTHER INFORMATION: X= N, T or S
<220> FEATURE:
<221> NAME/KEY: MISC_FEATURE
<222> LOCATION: (96)..(96)
<223> OTHER INFORMATION: X= I or F
<220> FEATURE:
<221> NAME/KEY: MISC_FEATURE
<222> LOCATION: (97)..(97)
<223> OTHER INFORMATION: X= K, N, A, or T
<220> FEATURE:
```

```
<221> NAME/KEY: MISC_FEATURE
<222> LOCATION: (101)..(101)
<223> OTHER INFORMATION: X= Q, K or E
<220> FEATURE:
<221> NAME/KEY: MISC_FEATURE
<222> LOCATION: (104)..(104)
<223> OTHER INFORMATION: X= V, I or K
<220> FEATURE:
<221> NAME/KEY: MISC_FEATURE
<222> LOCATION: (105)..(105)
<223> OTHER INFORMATION: X= H or R
<220> FEATURE:
<221> NAME/KEY: MISC_FEATURE
<222> LOCATION: (112)..(112)
<223> OTHER INFORMATION: X= N or Y
<220> FEATURE:
<221> NAME/KEY: MISC_FEATURE
<222> LOCATION: (113)..(113)
<223> OTHER INFORMATION: X= = T, S, P, L or A
<220> FEATURE:
<221> NAME/KEY: MISC_FEATURE
<222> LOCATION: (114)..(114)
<223> OTHER INFORMATION: X= = S or P

<400> SEQUENCE: 1

Xaa Trp Xaa Xaa Val Xaa Xaa Asp Leu Xaa Xaa Ile Xaa Xaa Leu Xaa
1               5                   10                  15

Xaa Xaa Xaa His Xaa Asp Xaa Thr Leu Tyr Thr Xaa Ser Xaa Xaa His
                20                  25                  30

Pro Xaa Cys Lys Xaa Thr Xaa Met Xaa Cys Phe Leu Leu Glu Leu Xaa
            35                  40                  45

Val Ile Xaa Xaa Glu Xaa Xaa Xaa Xaa Xaa Xaa Xaa Xaa Xaa Xaa Xaa
        50                  55                  60

Asn Xaa Xaa Xaa Leu Ala Asn Xaa Xaa Leu Xaa Xaa Xaa Xaa Xaa Xaa
65                  70                  75                  80

Xaa Glu Xaa Gly Cys Lys Xaa Cys Glu Glu Leu Glu Xaa Xaa Xaa Xaa
            85                  90                  95

Xaa Glu Phe Leu Xaa Ser Phe Xaa Xaa Ile Val Gln Met Phe Ile Xaa
            100                 105                 110

Xaa Xaa

<210> SEQ ID NO 2
<211> LENGTH: 114
<212> TYPE: PRT
<213> ORGANISM: Artificial Sequence
<220> FEATURE:
<223> OTHER INFORMATION: primate uinterleukin 15 consensus sequence
<220> FEATURE:
<221> NAME/KEY: MISC_FEATURE
<222> LOCATION: (1)..(1)
<223> OTHER INFORMATION: X = N or I
<220> FEATURE:
<221> NAME/KEY: MISC_FEATURE
<222> LOCATION: (4)..(4)
<223> OTHER INFORMATION: X = N or D
<220> FEATURE:
<221> NAME/KEY: MISC_FEATURE
<222> LOCATION: (10)..(10)
<223> OTHER INFORMATION: X = K or R
<220> FEATURE:
<221> NAME/KEY: MISC_FEATURE
<222> LOCATION: (11)..(11)
<223> OTHER INFORMATION: X = K or R
<220> FEATURE:
<221> NAME/KEY: MISC_FEATURE
<222> LOCATION: (13)..(13)
<223> OTHER INFORMATION: X = E or Q
<220> FEATURE:
<221> NAME/KEY: MISC_FEATURE
<222> LOCATION: (16)..(16)
```

```
<223> OTHER INFORMATION: X = I or T
<220> FEATURE:
<221> NAME/KEY: MISC_FEATURE
<222> LOCATION: (19)..(19)
<223> OTHER INFORMATION: X = M or I
<220> FEATURE:
<221> NAME/KEY: MISC_FEATURE
<222> LOCATION: (30)..(30)
<223> OTHER INFORMATION: X = D or G
<220> FEATURE:
<221> NAME/KEY: MISC_FEATURE
<222> LOCATION: (31)..(31)
<223> OTHER INFORMATION: X = V or I
<220> FEATURE:
<221> NAME/KEY: MISC_FEATURE
<222> LOCATION: (34)..(34)
<223> OTHER INFORMATION: X = S or R
<220> FEATURE:
<221> NAME/KEY: MISC_FEATURE
<222> LOCATION: (52)..(52)
<223> OTHER INFORMATION: X = L or H
<220> FEATURE:
<221> NAME/KEY: MISC_FEATURE
<222> LOCATION: (55)..(55)
<223> OTHER INFORMATION: X = G or N
<220> FEATURE:
<221> NAME/KEY: MISC_FEATURE
<222> LOCATION: (56)..(56)
<223> OTHER INFORMATION: X = D or N
<220> FEATURE:
<221> NAME/KEY: MISC_FEATURE
<222> LOCATION: (57)..(57)
<223> OTHER INFORMATION: X = A or T
<220> FEATURE:
<221> NAME/KEY: MISC_FEATURE
<222> LOCATION: (58)..(58)
<223> OTHER INFORMATION: X = S, N or D
<220> FEATURE:
<221> NAME/KEY: MISC_FEATURE
<222> LOCATION: (60)..(60)
<223> OTHER INFORMATION: X = H or N
<220> FEATURE:
<221> NAME/KEY: MISC_FEATURE
<222> LOCATION: (63)..(63)
<223> OTHER INFORMATION: X = V or I
<220> FEATURE:
<221> NAME/KEY: MISC_FEATURE
<222> LOCATION: (67)..(67)
<223> OTHER INFORMATION: X = I or L
<220> FEATURE:
<221> NAME/KEY: MISC_FEATURE
<222> LOCATION: (72)..(72)
<223> OTHER INFORMATION: X = N or R
<220> FEATURE:
<221> NAME/KEY: MISC_FEATURE
<222> LOCATION: (73)..(73)
<223> OTHER INFORMATION: X =S or I
<220> FEATURE:
<221> NAME/KEY: MISC_FEATURE
<222> LOCATION: (76)..(76)
<223> OTHER INFORMATION: X =S or A
<220> FEATURE:
<221> NAME/KEY: MISC_FEATURE
<222> LOCATION: (79)..(79)
<223> OTHER INFORMATION: X =N or T
<220> FEATURE:
<221> NAME/KEY: MISC_FEATURE
<222> LOCATION: (80)..(80)
<223> OTHER INFORMATION: X =V or I
<220> FEATURE:
<221> NAME/KEY: MISC_FEATURE
<222> LOCATION: (93)..(93)
<223> OTHER INFORMATION: X =E or K
<220> FEATURE:
<221> NAME/KEY: MISC_FEATURE
<222> LOCATION: (112)..(112)
<223> OTHER INFORMATION: X = N or Y
<220> FEATURE:
<221> NAME/KEY: MISC_FEATURE
```

```
<222> LOCATION: (113)..(113)
<223> OTHER INFORMATION: X = T or A

<400> SEQUENCE: 2

Xaa Trp Val Xaa Val Ile Ser Asp Leu Xaa Xaa Ile Xaa Asp Leu Xaa
1               5                   10                  15

Gln Ser Xaa His Ile Asp Ala Thr Leu Tyr Thr Glu Ser Xaa Xaa His
            20                  25                  30

Pro Xaa Cys Lys Val Thr Ala Met Lys Cys Phe Leu Leu Glu Leu Gln
        35                  40                  45

Val Ile Ser Xaa Glu Ser Xaa Xaa Xaa Xaa Ile Xaa Asp Thr Xaa Glu
    50                  55                  60

Asn Leu Xaa Ile Leu Ala Asn Xaa Xaa Leu Ser Xaa Asn Gly Xaa Xaa
65                  70                  75                  80

Thr Glu Ser Gly Cys Lys Glu Cys Glu Glu Leu Glu Xaa Lys Asn Ile
                85                  90                  95

Lys Glu Phe Leu Gln Ser Phe Val His Ile Val Gln Met Phe Ile Xaa
            100                 105                 110

Xaa Ser

<210> SEQ ID NO 3
<211> LENGTH: 114
<212> TYPE: PRT
<213> ORGANISM: Homo sapiens
<220> FEATURE:
<221> NAME/KEY: VARIANT
<222> LOCATION: (93)..(93)
<223> OTHER INFORMATION: X= E or K

<400> SEQUENCE: 3

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Xaa Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 4
<211> LENGTH: 61
<212> TYPE: PRT
<213> ORGANISM: Artificial Sequence
<220> FEATURE:
<223> OTHER INFORMATION: mammalian sushi domain consensus sequence
<220> FEATURE:
<221> NAME/KEY: MISC_FEATURE
<222> LOCATION: (3)..(3)
<223> OTHER INFORMATION: X= P or A
<220> FEATURE:
<221> NAME/KEY: MISC_FEATURE
<222> LOCATION: (5)..(5)
<223> OTHER INFORMATION: X= M or V
<220> FEATURE:
```

```
<221> NAME/KEY: MISC_FEATURE
<222> LOCATION: (7)..(7)
<223> OTHER INFORMATION: X= V or I
<220> FEATURE:
<221> NAME/KEY: MISC_FEATURE
<222> LOCATION: (13)..(13)
<223> OTHER INFORMATION: X= W, R or Q
<220> FEATURE:
<221> NAME/KEY: MISC_FEATURE
<222> LOCATION: (16)..(16)
<223> OTHER INFORMATION: X= S or N
<220> FEATURE:
<221> NAME/KEY: MISC_FEATURE
<222> LOCATION: (19)..(19)
<223> OTHER INFORMATION: X= L or V
<220> FEATURE:
<221> NAME/KEY: MISC_FEATURE
<222> LOCATION: (20)..(20)
<223> OTHER INFORMATION: X= Y, H or N
<220> FEATURE:
<221> NAME/KEY: MISC_FEATURE
<222> LOCATION: (26)..(26)
<223> OTHER INFORMATION: X= I or V
<220> FEATURE:
<221> NAME/KEY: MISC_FEATURE
<222> LOCATION: (39)..(39)
<223> OTHER INFORMATION: X= S or T
<220> FEATURE:
<221> NAME/KEY: MISC_FEATURE
<222> LOCATION: (41)..(41)
<223> OTHER INFORMATION: X=T or I
<220> FEATURE:
<221> NAME/KEY: MISC_FEATURE
<222> LOCATION: (45)..(45)
<223> OTHER INFORMATION: X=T or I
<220> FEATURE:
<221> NAME/KEY: MISC_FEATURE
<222> LOCATION: (45)..(45)
<223> OTHER INFORMATION: X= L or I
<220> FEATURE:
<221> NAME/KEY: MISC_FEATURE
<222> LOCATION: (48)..(48)
<223> OTHER INFORMATION: X= A or N
<220> FEATURE:
<221> NAME/KEY: MISC_FEATURE
<222> LOCATION: (51)..(51)
<223> OTHER INFORMATION: X= V or A
<220> FEATURE:
<221> NAME/KEY: MISC_FEATURE
<222> LOCATION: (53)..(53)
<223> OTHER INFORMATION: X= H or Y

<400> SEQUENCE: 4

Cys Pro Xaa Pro Xaa Ser Xaa Glu His Ala Asp Ile Xaa Val Lys Xaa
1               5                   10                  15

Tyr Ser Xaa Xaa Ser Arg Glu Arg Tyr Xaa Cys Asn Ser Gly Phe Lys
            20                  25                  30

Arg Lys Ala Gly Thr Ser Xaa Leu Xaa Glu Cys Val Xaa Asn Lys Xaa
        35                  40                  45

Thr Asn Xaa Ala Xaa Trp Thr Thr Pro Ser Leu Lys Cys
    50                  55                  60

<210> SEQ ID NO 5
<211> LENGTH: 64
<212> TYPE: PRT
<213> ORGANISM: Artificial Sequence
<220> FEATURE:
<223> OTHER INFORMATION: enlarged mammalian sushi domain consensus
      sequence
<220> FEATURE:
<221> NAME/KEY: MISC_FEATURE
<222> LOCATION: (1)..(1)
<223> OTHER INFORMATION: X= T, V or I
<220> FEATURE:
```

<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (9)..(9)
<223> OTHER INFORMATION: X= V or I
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (18)..(18)
<223> OTHER INFORMATION: X= S or N
<220> FEATURE:
<221> NAME/KEY: MISC_FEATURE
<222> LOCATION: (21)..(21)
<223> OTHER INFORMATION: X=L or V
<220> FEATURE:
<221> NAME/KEY: MISC_FEATURE
<222> LOCATION: (22)..(22)
<223> OTHER INFORMATION: X=Y, H or N
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (41)..(41)
<223> OTHER INFORMATION: X= S or T
<220> FEATURE:
<221> NAME/KEY: MISC_FEATURE
<222> LOCATION: (43)..(43)
<223> OTHER INFORMATION: X= T or I
<220> FEATURE:
<221> NAME/KEY: MISC_FEATURE
<222> LOCATION: (47)..(47)
<223> OTHER INFORMATION: X= L or I
<220> FEATURE:
<221> NAME/KEY: MISC_FEATURE
<222> LOCATION: (50)..(50)
<223> OTHER INFORMATION: X= A or N
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y

<400> SEQUENCE: 5

Xaa Thr Cys Pro Xaa Pro Xaa Ser Xaa Glu His Ala Asp Ile Xaa Val
1               5                   10                  15

Lys Xaa Tyr Ser Xaa Xaa Ser Arg Glu Arg Tyr Xaa Cys Asn Ser Gly
                20                  25                  30

Phe Lys Arg Lys Ala Gly Thr Ser Xaa Leu Xaa Glu Cys Val Xaa Asn
            35                  40                  45

Lys Xaa Thr Asn Xaa Ala Xaa Trp Thr Thr Pro Ser Leu Lys Cys Ile
    50                  55                  60

<210> SEQ ID NO 6
<211> LENGTH: 61
<212> TYPE: PRT
<213> ORGANISM: Artificial Sequence
<220> FEATURE:
<223> OTHER INFORMATION: primate sushi domain consensus sequence
<220> FEATURE:
<221> NAME/KEY: MISC_FEATURE

```
<222> LOCATION: (3)..(3)
<223> OTHER INFORMATION: X= P or A
<220> FEATURE:
<221> NAME/KEY: MISC_FEATURE
<222> LOCATION: (5)..(5)
<223> OTHER INFORMATION: X= M or V
<220> FEATURE:
<221> NAME/KEY: MISC_FEATURE
<222> LOCATION: (13)..(13)
<223> OTHER INFORMATION: X= W, R or Q
<220> FEATURE:
<221> NAME/KEY: MISC_FEATURE
<222> LOCATION: (20)..(20)
<223> OTHER INFORMATION: X= Y or H
<220> FEATURE:
<221> NAME/KEY: MISC_FEATURE
<222> LOCATION: (26)..(26)
<223> OTHER INFORMATION: X= I or V
<220> FEATURE:
<221> NAME/KEY: MISC_FEATURE
<222> LOCATION: (51)..(51)
<223> OTHER INFORMATION: X= V or A
<220> FEATURE:
<221> NAME/KEY: MISC_FEATURE
<222> LOCATION: (53)..(53)
<223> OTHER INFORMATION: X= V or A

<400> SEQUENCE: 6

Cys Pro Xaa Pro Xaa Ser Val Glu His Ala Asp Ile Xaa Val Lys Ser
1               5                   10                  15

Tyr Ser Leu Xaa Ser Arg Glu Arg Tyr Xaa Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Xaa Ala Xaa Trp Thr Thr Pro Ser Leu Lys Cys
    50                  55                  60

<210> SEQ ID NO 7
<211> LENGTH: 63
<212> TYPE: PRT
<213> ORGANISM: Artificial Sequence
<220> FEATURE:
<223> OTHER INFORMATION: enlarged primate sushi domain consensus
      sequence
<220> FEATURE:
<221> NAME/KEY: MISC_FEATURE
<222> LOCATION: (1)..(1)
<223> OTHER INFORMATION: X= V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (22)..(22)
<223> OTHER INFORMATION: X= Y or H
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (53)..(53)
<223> OTHER INFORMATION: X=V or A
<220> FEATURE:
<221> NAME/KEY: MISC_FEATURE
```

<222> LOCATION: (55)..(55)
<223> OTHER INFORMATION: X=H or Y

<400> SEQUENCE: 7

Xaa Thr Cys Pro Xaa Pro Xaa Ser Val Glu His Ala Asp Ile Xaa Val
1               5                   10                  15

Lys Ser Tyr Ser Leu Xaa Ser Arg Glu Arg Tyr Xaa Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Xaa Ala Xaa Trp Thr Thr Pro Ser Leu Lys Cys
            50                  55                  60

<210> SEQ ID NO 8
<211> LENGTH: 61
<212> TYPE: PRT
<213> ORGANISM: Homo sapiens

<400> SEQUENCE: 8

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
            35                  40                  45

Thr Asn Val Ala His Trp Thr Thr Pro Ser Leu Lys Cys
            50                  55                  60

<210> SEQ ID NO 9
<211> LENGTH: 64
<212> TYPE: PRT
<213> ORGANISM: Homo sapiens

<400> SEQUENCE: 9

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
            50                  55                  60

<210> SEQ ID NO 10
<211> LENGTH: 77
<212> TYPE: PRT
<213> ORGANISM: Artificial Sequence
<220> FEATURE:
<223> OTHER INFORMATION: mammalian sushi and domains consensus sequence
<220> FEATURE:
<221> NAME/KEY: MISC_FEATURE
<222> LOCATION: (1)..(1)
<223> OTHER INFORMATION: X= T, V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (9)..(9)

```
<223> OTHER INFORMATION: X= V or I
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (18)..(18)
<223> OTHER INFORMATION: X= S or N
<220> FEATURE:
<221> NAME/KEY: MISC_FEATURE
<222> LOCATION: (21)..(21)
<223> OTHER INFORMATION: X= L or V
<220> FEATURE:
<221> NAME/KEY: MISC_FEATURE
<222> LOCATION: (22)..(22)
<223> OTHER INFORMATION: X= Y, H or N
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (41)..(41)
<223> OTHER INFORMATION: X= S or T
<220> FEATURE:
<221> NAME/KEY: MISC_FEATURE
<222> LOCATION: (43)..(43)
<223> OTHER INFORMATION: X= T or I
<220> FEATURE:
<221> NAME/KEY: MISC_FEATURE
<222> LOCATION: (47)..(47)
<223> OTHER INFORMATION: X= L or I
<220> FEATURE:
<221> NAME/KEY: MISC_FEATURE
<222> LOCATION: (50)..(50)
<223> OTHER INFORMATION: X=A or N
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (68)..(68)
<223> OTHER INFORMATION: X=A, S or L
<220> FEATURE:
<221> NAME/KEY: MISC_FEATURE
<222> LOCATION: (70)..(70)
<223> OTHER INFORMATION: X= V, A, S or T
<220> FEATURE:
<221> NAME/KEY: MISC_FEATURE
<222> LOCATION: (71)..(71)
<223> OTHER INFORMATION: X= H or R
<220> FEATURE:
<221> NAME/KEY: MISC_FEATURE
<222> LOCATION: (72)..(72)
<223> OTHER INFORMATION: X= Q or H
<220> FEATURE:
<221> NAME/KEY: MISC_FEATURE
<222> LOCATION: (73)..(73)
<223> OTHER INFORMATION: X= R, S or K
<220> FEATURE:
<221> NAME/KEY: MISC_FEATURE
<222> LOCATION: (75)..(75)
<223> OTHER INFORMATION: X= A, V or P
<220> FEATURE:
<221> NAME/KEY: MISC_FEATURE
<222> LOCATION: (76)..(76)
<223> OTHER INFORMATION: X= P or S
<220> FEATURE:
<221> NAME/KEY: MISC_FEATURE
```

```
<222> LOCATION: (77)..(77)
<223> OTHER INFORMATION: X= P or T

<400> SEQUENCE: 10

Xaa Thr Cys Pro Xaa Pro Xaa Ser Xaa Glu His Ala Asp Ile Xaa Val
1               5                   10                  15

Lys Xaa Tyr Ser Xaa Xaa Ser Arg Glu Arg Tyr Xaa Cys Asn Ser Gly
            20                  25                  30

Phe Lys Arg Lys Ala Gly Thr Ser Xaa Leu Xaa Glu Cys Val Xaa Asn
        35                  40                  45

Lys Xaa Thr Asn Xaa Ala Xaa Trp Thr Thr Pro Ser Leu Lys Cys Ile
    50                  55                  60

Arg Asp Pro Xaa Leu Xaa Xaa Xaa Xaa Pro Xaa Xaa Xaa
65              70                  75

<210> SEQ ID NO 11
<211> LENGTH: 77
<212> TYPE: PRT
<213> ORGANISM: Artificial Sequence
<220> FEATURE:
<223> OTHER INFORMATION: primate sushi and domains consensus sequence
<220> FEATURE:
<221> NAME/KEY: MISC_FEATURE
<222> LOCATION: (1)..(1)
<223> OTHER INFORMATION: X= V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (22)..(22)
<223> OTHER INFORMATION: X= Y or H
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (68)..(68)
<223> OTHER INFORMATION: X= A, S or L
<220> FEATURE:
<221> NAME/KEY: MISC_FEATURE
<222> LOCATION: (70)..(70)
<223> OTHER INFORMATION: X= V, A or T
<220> FEATURE:
<221> NAME/KEY: MISC_FEATURE
<222> LOCATION: (71)..(71)
<223> OTHER INFORMATION: X= H or R
<220> FEATURE:
<221> NAME/KEY: MISC_FEATURE
<222> LOCATION: (75)..(75)
<223> OTHER INFORMATION: X= A or V

<400> SEQUENCE: 11

Xaa Thr Cys Pro Xaa Pro Xaa Ser Val Glu His Ala Asp Ile Xaa Val
```

```
                1               5                   10                  15
Lys Ser Tyr Ser Leu Xaa Ser Arg Glu Arg Tyr Xaa Cys Asn Ser Gly
                20                  25                  30

Phe Lys Arg Lys Ala Gly Thr Ser Leu Thr Glu Cys Val Leu Asn
            35                  40                  45

Lys Ala Thr Asn Xaa Ala Xaa Trp Thr Thr Pro Ser Leu Lys Cys Ile
        50                  55                  60

Arg Asp Pro Xaa Leu Xaa Xaa Gln Arg Pro Xaa Pro Pro
65                  70                  75
```

<210> SEQ ID NO 12
<211> LENGTH: 77
<212> TYPE: PRT
<213> ORGANISM: Homo sapiens

<400> SEQUENCE: 12

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Ala Leu Val His Gln Arg Pro Ala Pro Pro
65                  70                  75
```

<210> SEQ ID NO 13
<211> LENGTH: 20
<212> TYPE: PRT
<213> ORGANISM: Artificial Sequence
<220> FEATURE:
<223> OTHER INFORMATION: peptidic linker

<400> SEQUENCE: 13

```
Ser Gly Gly Ser Gly Gly Gly Gly Ser Gly Gly Ser Gly Gly Gly
1               5                   10                  15

Gly Ser Leu Gln
            20
```

<210> SEQ ID NO 14
<211> LENGTH: 20
<212> TYPE: PRT
<213> ORGANISM: Artificial Sequence
<220> FEATURE:
<223> OTHER INFORMATION: peptidic linker

<400> SEQUENCE: 14

```
Ser Gly Gly Ser Gly Gly Gly Gly Ser Gly Gly Ser Gly Gly Gly
1               5                   10                  15

Gly Ser Gly Gly
            20
```

<210> SEQ ID NO 15
<211> LENGTH: 21
<212> TYPE: PRT
<213> ORGANISM: Artificial Sequence
<220> FEATURE:
<223> OTHER INFORMATION: peptidic linker

<400> SEQUENCE: 15

-continued

Ser Gly Gly Gly Ser Gly Gly Gly Ser Gly Gly Gly Ser Gly
1               5                   10                  15

Gly Gly Ser Leu Gln
            20

<210> SEQ ID NO 16
<211> LENGTH: 211
<212> TYPE: PRT
<213> ORGANISM: Artificial Sequence
<220> FEATURE:
<223> OTHER INFORMATION: RLI2

<400> SEQUENCE: 16

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

Arg Asp Pro Ala Leu Val His Gln Arg Pro Ala Pro Pro Ser Gly Gly
65                  70                  75                  80

Ser Gly Gly Gly Ser Gly Gly Gly Ser Gly Gly Gly Ser Gly
                85                  90                  95

Gly Asn Trp Val Asn Val Ile Ser Asp Leu Lys Lys Ile Glu Asp Leu
                100                 105                 110

Ile Gln Ser Met His Ile Asp Ala Thr Leu Tyr Thr Glu Ser Asp Val
            115                 120                 125

His Pro Ser Cys Lys Val Thr Ala Met Lys Cys Phe Leu Leu Glu Leu
        130                 135                 140

Gln Val Ile Ser Leu Glu Ser Gly Asp Ala Ser Ile His Asp Thr Val
145                 150                 155                 160

Glu Asn Leu Ile Ile Leu Ala Asn Asn Ser Leu Ser Ser Asn Gly Asn
                165                 170                 175

Val Thr Glu Ser Gly Cys Lys Glu Cys Glu Glu Leu Glu Glu Lys Asn
            180                 185                 190

Ile Lys Glu Phe Leu Gln Ser Phe Val His Ile Val Gln Met Phe Ile
        195                 200                 205

Asn Thr Ser
    210

<210> SEQ ID NO 17
<211> LENGTH: 211
<212> TYPE: PRT
<213> ORGANISM: Artificial Sequence
<220> FEATURE:
<223> OTHER INFORMATION: RLI1

<400> SEQUENCE: 17

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
                20                  25                  30

Phe Lys Arg Lys Ala Gly Thr Ser Ser Leu Thr Glu Cys Val Leu Asn
            35                  40                  45

Lys Ala Thr Asn Val Ala His Trp Thr Thr Pro Ser Leu Lys Cys Ile
        50                  55                  60

-continued

```
Arg Asp Pro Ala Leu Val His Gln Arg Pro Ala Pro Pro Ser Gly Gly
 65              70                  75                  80

Ser Gly Gly Gly Gly Ser Gly Gly Gly Ser Gly Gly Gly Gly Ser Leu
             85                  90                  95

Gln Asn Trp Val Asn Val Ile Ser Asp Leu Lys Lys Ile Glu Asp Leu
            100                 105                 110

Ile Gln Ser Met His Ile Asp Ala Thr Leu Tyr Thr Glu Ser Asp Val
            115                 120                 125

His Pro Ser Cys Lys Val Thr Ala Met Lys Cys Phe Leu Leu Glu Leu
            130                 135                 140

Gln Val Ile Ser Leu Glu Ser Gly Asp Ala Ser Ile His Asp Thr Val
145                 150                 155                 160

Glu Asn Leu Ile Ile Leu Ala Asn Asn Ser Leu Ser Ser Asn Gly Asn
                165                 170                 175

Val Thr Glu Ser Gly Cys Lys Glu Cys Glu Glu Leu Glu Glu Lys Asn
                180                 185                 190

Ile Lys Glu Phe Leu Gln Ser Phe Val His Ile Val Gln Met Phe Ile
            195                 200                 205

Asn Thr Ser
        210
```